United States Patent [19]
Hirose et al.

[11] Patent Number: 4,479,954
[45] Date of Patent: Oct. 30, 1984

[54] PIPERAZINE SUBSTITUTED CARBOXAMIDE DERIVATIVES, COMPOSITIONS AND METHOD OF USE

[75] Inventors: Noriyasu Hirose; Shigeru Souda; Kazutoshi Miyake, all of Tokyo; Shizuo Kuriyama, Saitama; Kazuyasu Usuki, Tokyo; Yasuhiro Akiyama, Tokyo; Naoko Sakabe, Tokyo; Hidetoshi Kawashima, Ibaraki, all of Japan

[73] Assignee: Eisai Co., Ltd., Tokyo, Japan

[21] Appl. No.: 382,792

[22] Filed: May 27, 1982

[30] Foreign Application Priority Data

May 29, 1981 [JP] Japan .................................. 56-80866

[51] Int. Cl.³ .................... A61K 31/505; C07D 521/00
[52] U.S. Cl. .................... 424/251; 424/250;
260/239 BF; 544/295; 544/360; 544/361;
544/362; 544/372; 544/373; 544/368
[58] Field of Search ............... 544/372, 373, 360, 361,
544/362, 295; 542/413; 260/239 BF; 424/250,
251

[56] References Cited

U.S. PATENT DOCUMENTS

| 3,126,395 | 3/1964 | Kitahonoki et al. | 544/372 |
|---|---|---|---|
| 3,126,396 | 3/1964 | Kitahonoki et al. | 544/372 |
| 3,198,798 | 8/1965 | Zenitz et al. | 544/373 |
| 3,563,986 | 2/1971 | Frankus et al. | 544/373 |
| 3,579,524 | 5/1971 | van Dyke, Jr. | 544/373 |
| 3,850,922 | 11/1974 | Matuo et al. | 544/372 |
| 3,936,449 | 2/1976 | Matuo et al. | 544/372 |
| 3,980,667 | 9/1976 | Partyka et al. | 544/372 |
| 4,018,767 | 4/1977 | Buyniski et al. | 544/372 |
| 4,070,465 | 1/1978 | Wade et al. | 544/372 |
| 4,139,533 | 2/1979 | Buchanan et al. | 544/372 |

Primary Examiner—Richard L. Raymond
Assistant Examiner—James H. Turnipseed
Attorney, Agent, or Firm—Wenderoth, Lind & Ponack

[57] ABSTRACT

The carboximide derivatives of the formula:

and pharmaceutically acceptable salts thereof; wherein X represents a group of the formula:

(continued on next page.)

Z represents a hydrogen atom or a group of the formula:

wherein R represents an alkyl group, an aralkyl group, an aryl group, a cycloalkyl group, an alkenyl group, an arylalkenyl group, a pyridyl group or a substituted amino group; Y represents an alkyl group, an aralkyl group, an aryl group, a substituted or unsubstituted pyridyl group, a substituted or unsubstituted pyrimidyl group or a benzothiazolyl group; and m represents an integer of 2 or 3 and processes for the production thereof. The derivatives and their salts possess hypoglycemic activity and are useful for treating diabetes.

43 Claims, No Drawings

PIPERAZINE SUBSTITUTED CARBOXAMIDE DERIVATIVES, COMPOSITIONS AND METHOD OF USE

BACKGROUND OF THE INVENTION

1. Field of the Invention

The present invention relates to novel carboximide derivatives having excellent medicinal effects, to processes for their production and to medicines containing same.

More particularly, this invention relates to carboximide derivatives of the formula:

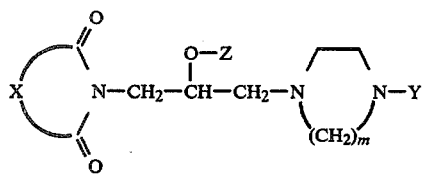

[I]

and acid addition salts thereof;
wherein X represents a group of the formula:

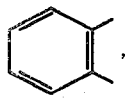

a group of the formula: (cyclohexyl), a group of the formula: (cyclohexenyl), a group of the formula: (norbornyl), a group of the formula: (norbornenyl), a group of the formula: (bicyclic), a group of the formula: (bicyclic), a group of the formula: (phenyl-cyclohexyl fused), a group of the formula: (pyridyl) 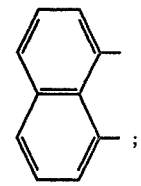, a group of the formula: (cyclopentyl), a group of the formula:  or a group of the formula: (naphthyl);

Z represents a hydrogen atom or a group of the formula:

$$-\overset{O}{\underset{\|}{C}}-R$$

wherein R represents an alkyl group, an aralkyl group, an aryl group, a cycloalkyl group, an alkenyl group, an arylalkenyl group, a pyridyl group or a substituted amino group; Y represents an alkyl group, an aralkyl group, an aryl group, a substituted or unsubstituted pyridyl group, a substituted or unsubstituted pyrimidyl group or a benzothiazolyl group; and m represents an integer of 2 or 3, to processes for their production, and to medicines containing same.

DESCRIPTION OF THE PRIOR ART

The carboximide derivatives provided by the present invention are novel compounds which have not yet been disclosed in any literature, and it has now been discovered that these compounds unexpectedly have hypoglycemic activity and are useful as treating agents for diabetes. In other words, the carboximide derivatives provided by the present invention are remarkably different in structure from the conventionally and widely employed sulfonyl urea agents, biguanide agents, etc.

SUMMARY OF THE INVENTION

Accordingly, an object of the present invention is to provide novel carboximide derivatives useful as treating agents for diabetes.

Another object of the present invention is to provide processes for the production of novel carboximide derivatives useful as treating agents for diabetes.

Still another object of the present invention is to provide novel treating agents for diabetes.

DETAILED DESCRIPTION OF THE PREFERRED EMBODIMENTS

In the definition of X in the formula above, where X represents a group of the formula:

, a group of the formula: 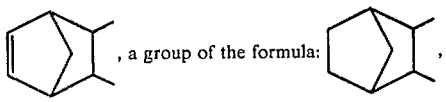, a group of the formula: 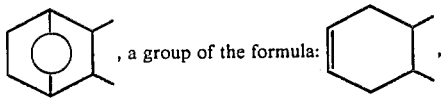, a group of the formula:

, a group of the formula: or a group of the formula:

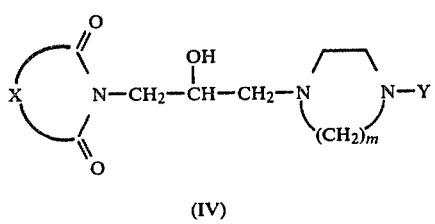, these groups may exist in stereoisomeric forms, and often exist as exo and endo forms, and cis and trans forms, and therefore, the present invention encompasses all such stereoisomers.

Further, the compounds of the present invention may easily form acid addition salts by reacting with a pharmaceutically acceptable inorganic acid or organic acid. Examples of such an inorganic acid include hydrochloric acid, hydrobromic acid, hydroiodic acid, sulfulic acid etc., and examples of such an organic acid include maleic acid, fumaric acid, succinic acid, acetic acid, malonic acid, citric acid, benzoic acid etc.

The compounds of the present invention may be produced by various routes, among which some representative examples commonly employed are described below:

[Preparative Process 1]

Where Z is a hydrogen atom:

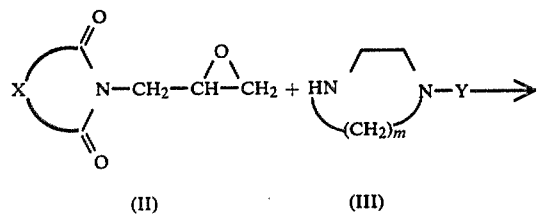

(II)            (III)

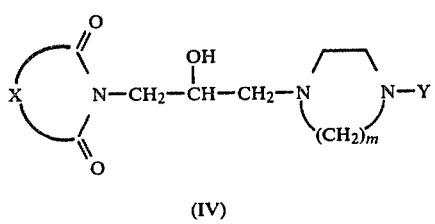

(IV)

wherein X, Y and m are as defined above.

That is, a compound of the formula (II) and a compound of the formula (III) are reacted to obtain a compound (IV) of the present invention.

This reaction may be carried out by appropriately selecting a solvent which does not participate in the reaction from, e.g., lower alcoholic solvents such as methanol, ethanol, propanol, isopropanol, butanol etc., 2-butanone, methyl isobutyl ketone etc.

In this process, the compound of the formula (II) employed as one starting material may be produced by, for example, the following process:

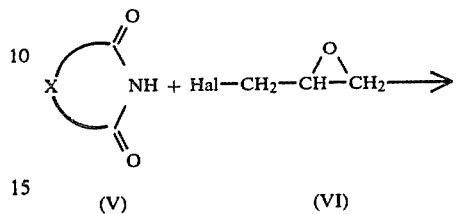

(V)             (VI)

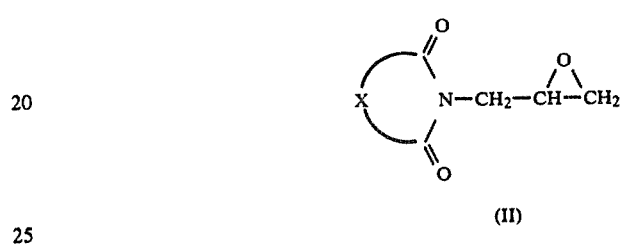

(II)

wherein X is as defined above, and Hal represents a halogen atom.

That is, a compound of the formula (V) and a compound of the formula (VI) are reacted to obtain a compound of the formula (II).

This reaction may be carried out by appropriately selecting a solvent which does not participate in the reaction from e.g. lower alcoholic solvents such as methanol, ethanol, propanol, isopropanol, butanol etc., benzenic solvents such as benzene, toluene, xylene etc., etheric solvents such as dioxane, tetrahydrofuran etc., dimethylformamide (DMF), dimethylsulfoxide (DMSO), methyl ethyl ketone, methyl isobutyl ketone, water etc. On reaction, it is also possible to add an acid removing agent such as potassium carbonate, sodium hydroxide, potassium hydroxide, triethylamine etc. to the reaction system.

[Preparative Process 2]

Where Z is other than a hydrogen atom, and R represents an alkyl group, an aralkyl group, an aryl group, a cycloalkyl group, a pyridyl group, an alkenyl group or an arylalkenyl group:

In this case, the desired compound may be obtained by esterifying the hydroxyl group of a compound of the formula:

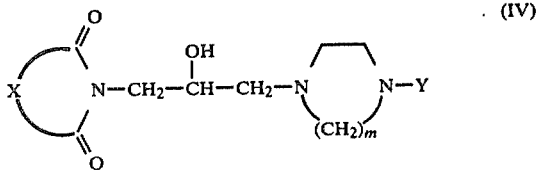

wherein X, Y and m are as defined above; which has been produced by either the [Preparative Process 1] or other process.

As a representative process, the above compound of the formula (IV) is reacted with a carboxylic acid of the formula: RCOOH (VII) or a reactive derivative thereof, wherein R represents an alkyl group, an aralkyl group, an aryl group, a cycloalkyl group, a pyridyl group, an alkenyl group or an arylalkenyl group in conventional manner to obtain the desired compound, ester (I).

The most preferred and conventionally employed process comprises reacting with RCOCl, i.e. an acid halide (VII), to readily obtain the desired compound (I). At this time, preferred results may be obtained by employing an acid removing agent such as triethylamine, potassium carbonate, sodium carbonate etc. As the solvent in this case, e.g. chloroform, dichloroethane, dioxane, tetrahydrofuran, dimethylformamide etc. may be employed.

[Preparative Process 3]

Where Z is other than a hydrogen atom, and R represents a substituted amino group:

The desired compound may be obtained by converting the hydroxyl group of the compound of the formula:

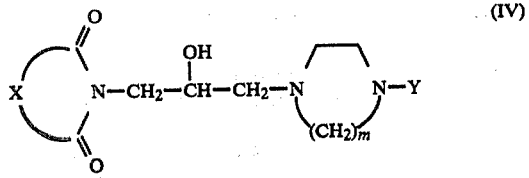 (IV)

wherein X, Y and m are as defined above, which has been produced by either the [Preparative Process 1] or other process, to a urethane group.

One representative process comprises reacting the above compound of the formula (IV) with an isocyanate of the formula $R_1NCO$ wherein $R_1$ represents an alkyl group or a cycloalkyl group in conventional manner to obtain the desired compound (I). As the solvent in this case, e.g. toluene, xylene, cumene, cymene etc. may be employed.

Representative compounds of the present invention are illustrated below, but it should be understood that the present invention is not restricted thereto. Although the compounds set forth below are expressed as free forms, it should of course be understood that they include acid addition salts formed with a pharmaceutically acceptable inorganic acid or organic acid.

N-[2-Hydroxy-3-{4-(2-pyridyl)piperazin-1-yl}propyl]-cis-cyclohex-4-ene-1,2-dicarboximide;
N-[2-acetoxy-3-{4-(2-pyridyl)piperazin-1-yl}propyl]cis-cyclohex-4-ene-1,2-dicarboximide;
N-[2-propionyloxy-3-{4-(2-pyridyl)piperazin-1-yl}propyl]cis-cyclohex-4-ene-1,2-dicarboximide;
N-[2-isobutyryloxy-3-{4-(2-pyridyl)piperazin-1-yl}propyl]cis-cyclohex-4-ene-1,2-dicarboximide;
N-[2-n-butanoyloxy-3-{4-(2-pyridyl)piperazin-1-yl}propyl]cis-cyclohex-4-ene-1,2-dicarboximide;
N-[2-n-hexanoyloxy-3-{4-(2-pyridyl)piperazin-1-yl}propyl]cis-cyclohex-4-ene-1,2-dicarboximide;
N-[2-n-heptanoyloxy-3-{4-(2-pyridyl)piperazin-1-yl}propyl]cis-cyclohex-4-ene-1,2-dicarboximide;
N-[2-n-octanoyloxy-3-{4-(2-pyridyl)piperazin-1-yl}propyl]cis-cyclohex-4-ene-1,2-dicarboximide;
N-[2-n-nonanoyloxy-3-{4-(2-pyridyl)piperazin-1-yl}propyl]cis-cyclohex-4-ene-1,2-dicarboximide;
N-[2-n-decanoyloxy-3-{4-(2-pyridyl)piperazin-1-yl}propyl]cis-cyclohex-4-ene-1,2-dicarboximide;
N-[3-{4-(2-pyridyl)piperazin-1-yl}-2-n-undecanoyloxypropyl]cis-cyclohex-4-ene-1,2-dicarboximide;
N-[2-n-dodecanoyloxy-3-{4-(2-pyridyl)piperazin-1-yl}propyl]cis-cyclohex-4-ene-1,2-dicarboximide;
N-[2-n-tridecanoyloxy-3-{4-(2-pyridyl)piperazin-1-yl}propyl]cis-cyclohex-4-ene-1,2-dicarboximde;
N-[2-n-tetradecanoyloxy-3-{4-(2-pyridyl)piperazin-1-yl}propyl]cis-cyclohex-4-ene-1,2-dicarboximide;
N-[2-n-pentadecanoyloxy-3-{4-(2-pyridyl)piperazin-1-yl}propyl]cis-cyclohex-4-ene-1,2-dicarboximide;
N-[2-n-hexadecanoyloxy-3-{4-(2-pyridyl)piperazin-1-yl}propyl]cis-cyclohex-4-ene-1,2-dicarboximide;
N-[2-cyclohexylcarbonyloxy-3-{4-(2-pyridyl)piperazin-1-yl}propyl]cis-cyclohex-4-ene-1,2-dicarboximide;
N-[2-cyclopentylcarbonyloxy-3-{4-(2-pyridyl)piperazin-1-yl}propyl]cis-cyclohex-4-ene-1,2-dicarboximide;
N-[2-(3-phenylpropionyloxy)-3-{4-(2-pyridyl)piperazin-1-yl}propyl]cis-cyclohex-4-ene-1,2-dicarboximide;
N-[3-{4-(2-pyridyl)piperazin-1-yl}-2-(10-undecenoyloxy)propyl]cis-cyclohex-4-ene-1,2-dicarboximide;
N-[2-(trans-2-nonenoyloxy)-3-{4-(2-pyridyl)piperazin-1-yl}propyl]cis-cyclohex-4-ene-1,2-dicarboximide;
N-[2-benzoyloxy-3-{4-(2-pyridyl)piperazin-1-yl}propyl]cis-cyclohex-4-ene-1,2-dicarboximide;
N-[2-(4-methylbenzoyloxy)-3-{4-(2-pyridyl)piperazin-1-yl}propyl]cis-cyclohex-4-ene-1,2-dicarboximide;
N-[2-(2-methoxybenzoyloxy)-3-{4-(2-pyridyl)piperazin-1-yl}propyl]cis-cyclohex-4-ene-1,2-dicarboximide;
N-[2-n-butylaminocarbonyloxy-3-{4-(2-pyridyl)piperazin-1-yl}propyl]cis-cyclohex-4-ene-1,2-dicarboximide;
N-[2-cyclohexylaminocarbonyloxy-3-{4-(2-pyridyl)piperazin-1-yl}propyl]cis-cyclohex-4-ene-1,2-dicarboximide;
N-[2-nicotinyloxy-3-{4-(2-pyridyl)piperazin-1-yl}propyl]cis-cyclohex-4-ene-1,2-dicarboximide;
N-[2-n-decylaminocarbonyloxy-3-{4-(2-pyridyl)piperazin-1-yl}propyl]cis-cyclohex-4-ene-1,2-dicarboximide;
N-[2-cinnamoyloxy-3-{4-(2-pyridyl)piperazin-1-yl}propyl]cis-cyclohex-4-ene-1,2-dicarboximide;
N-[2-hydroxy-3-{4-(2-pyridyl)piperazin-1-yl}propyl]-cyclohexane-1,2-dicarboximide;
N-[2-acetoxy-3-{4-(2-pyridyl)piperazin-1-yl}propyl]cyclohexane-1,2-dicarboximide;
N-[2-isobutyryloxy-3-{4-(2-pyridyl)piperazin-1-yl}propyl]cyclohexane-1,2-dicarboximide;
N-[2-n-caproyloxy-3-{4-(2-pyridyl)piperazin-1-yl}propyl]cyclohexane-1,2-dicarboximide;
N-[2-cyclohexylcarbonyloxy-3-{4-(2-pyridyl)piperazin-1-yl}propyl]cycohexane-1,2-dicarboximide;
N-[2-n-decanoyloxy-3-{4-(2-pyridyl)piperazin-1-yl}propyl]cyclohexane-1,2-dicarboximide;
N-[2-palmitoyloxy-3-{4-(2-pyridyl)piperazin-1-yl}propyl]cyclohexane-1,2-dicarboximide;
N-[3-{4-(2-pyridyl)piperazin-1-yl}-2-(10-undecenoyloxy)propyl]cyclohexane-1,2-dicarboximide;
N-[2-nicotinyloxy-3-{4-(2-pyridyl)piperazin-1-yl}propyl]cyclohexane-1,2-dicarboximide;
N-[2-propionyloxy-3-{4-(2-pyridyl)piperazin-1-yl}propyl]cyclohexane-1,2-dicarboximide;
N-[2-n-butylaminocarbonyloxy-3-{4-(2-pyridyl)piperazin-1-yl}propyl]cyclohexane-1,2-dicarboximide;
N-[2-benzoyloxy-3-{4-(2-pyridyl)piperazin-1-yl}propyl]cyclohexane-1,2-dicarboximide;
N-[2-(trans-2-nonenoyloxy)-3-{4-(2-pyridyl)piperazin-1-yl}propyl]cyclohexane-1,2-dicarboximide;
N-[2-cinnamoyloxy-3-{4-(2-pyridyl)piperazin-1-yl}propyl]cyclohexane-1,2-dicarboximide;

N-[2-hydroxy-3-{4-(2-pyridyl)piperazin-1-yl}propyl]-succinimide;
N-[2-acetoxy-3-{4-(2-pyridyl)piperazin-1-yl}propyl]-succinimide;
N-[2-propionyloxy-3-{4-(2-pyridyl)piperazin-1-yl}propyl]succinimide;
N-[2-isobutyryloxy-3-{4-(2-pyridyl)piperazin-1-yl}propyl]succinimide;
N-[2-n-caproyloxy-3-{4-(2-pyridyl)piperazin-1-yl}propyl]succinimide;
N-[2-cyclohexylcarbonyloxy-3-{4-(2-pyridyl)piperazin-1-yl}propyl]succinimide;
N-[2-n-decanoyloxy-3-{4-(2-pyridyl)piperazin-1-yl}propyl]succinimide;
N-[2-palmitoyloxy-3-{4-(2-pyridyl)piperazin-1-yl}propyl]succinimide;
N-[3-{4-(2-pyridyl)piperazin-1-yl}-2-(10-undecenoyloxy)propyl]succinimide;
N-[2-(trans-2-nonenoyloxy)-3-{4-(2-pyridyl)piperazin-1-yl}propyl]succinimide;
N-[2-benzoyloxy-3-{4-(2-pyridyl)piperazin-1-yl}propyl]succinimide;
N-[2-n-octanoyloxy-3-{4-(2-pyridyl)piperazin-1-yl}propyl]succinimide;
N-[2-cinnamoyloxy-3-{4-(2-pyridyl)piperazin-1-yl}propyl]succinimide;
N-[2-n-decylaminocarbonyloxy-3-{4-(2-pyridyl)piperazin-1-yl}propyl]succinimide;
N-[2-hydroxy-3-{4-(2-pyridyl)piperazin-1-yl}propyl]endo-bicyclo[2,2,1]hept-5-ene-2,3-dicarboximide;
N-[2-acetoxy-3-{4-(2-pyridyl)piperazin-1-yl}propyl]endo-bicyclo[2,2,1]hept-5-ene-2,3-dicarboximide;
N-[2-propionyloxy-3-{4-(2-pyridyl)piperazin-1-yl}propyl]endo-bicyclo[2,2,1]hept-5-ene-2,3-dicarboximide;
N-[2-isobutyryloxy-3-{4-(2-pyridyl)piperazin-1-yl}propyl]endo-bicyclo[2,2,1]hept-5-ene-2,3-dicarboximide;
N-[2-n-caproyloxy-3-{4-(2-pyridyl)piperazin-1-yl}propyl]endo-bicyclo[2,2,1]hept-5-ene-2,3-dicarboximide;
N-[2-cyclohexylcarbonyloxy-3-{4-(2-pyridyl)piperazin-1-yl}propyl]endo-bicyclo[2,2,1]hept-5-ene-2,3-dicarboximide;
N-[2-n-decanoyloxy-3-{4-(2-pyridyl)piperazin-1-yl}propyl]endo-bicyclo[2,2,1]hept-5-ene-2,3-dicarboximide;
N-[2-(trans-2-nonenoyloxy)-3-{4-(2-pyridyl)piperazin-1-yl}propyl]endo-bicyclo[2,2,1]hept-5-ene-2,3-dicarboximide;
N-[2-n-butylaminocarbonyloxy-3-{4-(2-pyridyl)piperazin-1-yl}propyl]endo-bicyclo[2,2,1]hept-5-ene-2,3-dicarboximide;
N-[2-cyclohexylaminocarbonyloxy-3-{4-(2-pyridyl)piperazin-1-yl}propyl]endo-bicyclo[2,2,1]hept-5-ene-2,3-dicarboximide;
N-[2-nicotinyloxy-3-{4-(2-pyridyl)piperazin-1-yl}propyl]endo-bicyclo[2,2,1]hept-5-ene-2,3-dicarboximide;
N-[2-n-decylaminocarbonyloxy-3-{4-(2-pyridyl)piperazin-1-yl}propyl]endo-bicyclo[2,2,1]hept-5-ene-2,3-dicarboximide;
N-[2-cinnamoyloxy-3-{4-(2-pyridyl)piperazin-1-yl}propyl]endo-bicyclo[2,2,1]hept-5-ene-2,3-dicarboximide;
N-[2-n-octanoyloxy-3-{4-(2-pyridyl)piperazin-1-yl}propyl]endo-bicyclo[2,2,1]hept-5-ene-2,3-dicarboximide;
N-[3-{4-(2-pyridyl)piperazin-1-yl}-2-(10-undecenoyloxy)propyl]endo-bicyclo[2,2,1]hept-5-ene-2,3-dicarboximide;
N-[2-cinnamoyloxy-3-{4-(2-pyridyl)piperazin-1-yl}propyl]endo-bicyclo[2,2,1]hept-5-ene-2,3-dicarboximide;
N-[2-n-butanoyloxy-3-{4-(2-pyridyl)piperazin-1-yl}propyl]endo-bicyclo[2,2,1]hept-5-ene-2,3-dicarboximide;
N-[2-n-hexanoyloxy-3-{4-(2-pyridyl)piperazin-1-yl}propyl]endo-bicyclo[2,2,1]hept-5-ene-2,3-dicarboximide;
N-[2-n-heptanoyloxy-3-{4-(2-pyridyl)piperazin-1-yl}propyl]endo-bicyclo[2,2,1]hept-5-ene-2,3-dicarboximide;
N-[2-n-octanoyloxy-3-{4-(2-pyridyl)piperazin-1-yl}propyl]endo-bicyclo[2,2,1]hept-5-ene-2,3-dicarboximide;
N-[2-n-nonanoyloxy-3-{4-(2-pyridyl)piperazin-1-yl}propyl]endo-bicyclo[2,2,1]hept-5-ene-2,3-dicarboximide;
N-[2-n-decanoyloxy-3-{4-(2-pyridyl)piperazin-1-yl}propyl]endo-bicyclo[2,2,1]hept-5-ene-2,3-dicarboximide;
N-[2-n-undecanoyloxy-3-{4-(2-pyridyl)piperazin-1-yl}propyl]endo-bicyclo[2,2,1]hept-5-ene-2,3-dicarboximide;
N-[2-n-dodecanoyloxy-3-{4-(2-pyridyl)piperazin-1-yl}propyl]endo-bicyclo[2,2,1]hept-5-ene-2,3-dicarboximide;
N-[2-n-tridecanoyloxy-3-{4-(2-pyridyl)piperazin-1-yl}propyl]endo-bicyclo[2,2,1]hept-5-ene-2,3-dicarboximide;
N-[2-n-tetradecanoyloxy-3-{4-(2-pyridyl)piperazin-1-yl}propyl]endo-bicyclo[2,2,1]hept-5-ene-2,3-dicarboximide;
N-[2-n-pentadecanoyloxy-3-{4-(2-pyridyl)piperazin-1-yl}propyl]endo-bicyclo[2,2,1]hept-5-ene-2,3-dicarboximide;
N-[2-n-hexadecanoyloxy-3-{4-(2-pyridyl)piperazin-1-yl}propyl]endo-bicyclo[2,2,1]hept-5-ene-2,3-dicarboximide;
N-[3-{4-(2-pyridyl)piperazin-1-yl}-2-(10-undecenoyloxy)propyl]endo-bicyclo[2,2,1]hept-5-ene-2,3-dicarboximide;
N-[2-benzoyloxy-3-{4-(2-pyridyl)piperazin-1-yl}propyl]endo-bicyclo[2,2,1]hept-5-ene-2,3-dicarboximide;
N-[2-(3-phenylpropionyloxy)-3-{4-(2-pyridyl)piperazin-1-yl}propyl]endo-bicyclo[2,2,1]hept-5-ene-2,3-dicarboximide;
N-[2-(4-methoxybenzoyloxy)-3-{4-(2-pyridyl)piperazin-1-yl}propyl]endo-bicyclo[2,2,1]hept-5-ene-2,3-dicarboximide;
N-[2-(2-chlorobenzoyloxy)-3-{4-(2-pyrimidyl)piperazin-1-yl}propyl]endo-bicyclo[2,2,1]hept-5-ene-2,3-dicarboximide;
N-[2-hydroxy-3-{4-(2-pyridyl)piperazin-1-yl}propyl]exo-bicyclo[2,2,1]hept-5-ene-2,3-dicarboximide;
N-[2-benzoyloxy-3-{4-(2-pyridyl)piperazin-1-yl}propyl]exo-bicyclo[2,2,1]hept-5-ene-2,3-dicarboximide;
N-[2-hexanoyloxy-3-{4-(2-pyridyl)piperazin-1-yl}propyl]exo-bicyclo[2,2,1]hept-5-ene-2,3-dicarboximide;
N-[2-acetoxy-3-{4-(2-pyridyl)piperazin-1-yl}propyl]exo-bicyclo[2,2,1]hept-5-ene-2,3-dicarboximide;

N-[2-hydroxy-3-{4-(2-pyridyl)piperazin-1-yl}propyl]phthalimide;
N-[2-acetoxy-3-{4-(2-pyridyl)piperazin-1-yl}propyl]phthalimide;
N-[2-propionyloxy-3-{4-(2-pyridyl)piperazin-1-yl}propyl]phthalimide;
N-[2-isobutyryloxy-3-{4-(2-pyridyl)piperazin-1-yl}propyl]phthalimide;
N-[2-n-caproyloxy-3-{4-(2-pyridyl)piperazin-1-yl}propyl]phthalimide;
N-[2-cyclohexylcarbonyloxy-3-{4-(2-pyridyl)piperazin-1-yl}propyl]phthalimide;
N-[2-n-decanoyloxy-3-{4-(2-pyridyl)piperazin-1-yl}propyl]phthalimide;
N-[2-palmitoyloxy-3-{4-(2-pyridyl)piperazin-1-yl}propyl]phthalimide;
N-[3-{4-(2-pyridyl)piperazin-1-yl}-2-(10-undecenoyloxy)propyl]phthalimide;
N-[2-(trans-2-nonenoyloxy)-3-{4-(2-pyridyl)piperazin-1-yl}propyl]phthalimide;
N-[2-nicotinyloxy-3-{4-(2-pyridyl)piperazin-1-yl}propyl]phthalimide;
N-[2-benzoyloxy-3-{4-(2-pyridyl)piperazin-1-yl}propyl]phthalimide;
N-[2-n-octanoyloxy-3-{4-(2-pyridyl)piperazin-1-yl}propyl]phthalimide;
N-[2-cinnamoyloxy-3-{4-(2-pyridyl)piperazin-1-yl}propyl]phthalimide;
N-[2-n-butylaminocarbonyloxy-3-{4-(2-pyridyl)piperazin-1-yl}propyl]phthalimide;
N-[2-cyclohexylaminocarbonyloxy-3-{4-(2-pyridyl)piperazin-1-yl}propyl]phthalimide;
N-[2-benzoyloxy-3-{4-(2-pyridyl)piperazin-1-yl}propyl]phthalimide;
N-[2-hydroxy-3-{4-(2-pyridyl)piperazin-1-yl}propyl]endo-bicyclo[2,2,2]oct-5-ene-2,3-dicarboximide;
N-[2-n-caproyloxy-3-{4-(2-pyridyl)piperazin-1-yl}propyl]endo-bicyclo[2,2,2]oct-5-ene-2,3-dicarboximide;
N-[2-cyclohexylcarbonyloxy-3-{4-(2-pyridyl)piperazin-1-yl}propyl]endo-bicyclo[2,2,2]oct-5-ene-2,3-dicarboximide;
N-[2-hydroxy-3-{4-(2-pyridyl)piperazin-1-yl}propyl]endo-bicyclo[2,2,1]heptane-2,3-dicarboximide;
N-[2-n-caproyloxy-3-{4-(2-pyridyl)piperazin-1-yl}propyl]endo-bicyclo[2,2,1]heptane-2,3-dicarboximide;
N-[2-hydroxy-3-{4-(2-pyridyl)piperazin-1-yl}propyl]endo-7-oxabicyclo[2,2,1]heptane-2,3-dicarboximide;
N-[2-n-caproyloxy-3-{4-(2-pyridyl)piperazin-1-yl}propyl]endo-7-oxabicyclo[2,2,1]heptane-2,3-dicarboximide;
N-[2-cyclohexylcarbonyloxy-3-{4-(2-pyridyl)piperazin-1-yl}propyl]endo-7-oxabicyclo[2,2,1]]heptane-2,3-dicarboximide;
N-[2-n-hexadecanoyloxy-3-{4-(2-pyridyl)piperazin-1-yl}propyl]endo-7-oxabicyclo[2,2,1]heptane-2,3-dicarboxyimide;
N-[2-n-hexadecanoyloxy-3-{4-(2-pyridyl)piperazin-1-yl}propyl]endo-bicyclo[2,2,1]heptane-2,3-dicarboximide;
N-[2-hydroxy-3-{4-(2-pyrimidyl)piperazin-1-yl}propyl]cis-cyclohex-4-ene-1,2-dicarboximide;
N-[2-isobutyryloxy-3-{4-(2-pyrimidyl)piperazin-1-yl}propyl]cis-cyclohex-4-ene-1,2-dicarboximide;
N-[2-n-caproyloxy-3-{4-(2-pyrimidyl)piperazin-1-yl}propyl]cis-cyclohex-4-ene-1,2-dicarboximide;
N-[2-cyclohexylcarbonyloxy-3-{4-(2-pyrimidyl)piperazin-1-yl}propyl]cis-cyclohex-4-ene-1,2-dicarboximide;
N-[2-acetoxy-3-{4-(2-pyrimidyl)piperazin-1-yl}propyl]cis-cyclohex-4-ene-1,2-dicarboximide;
N-[2-benzoyloxy-3-{4-(2-pyrimidyl)piperazin-1-yl}propyl]cis-cyclohex-4-ene-1,2-dicarboximide;
N-[2-propionyloxy-3-{4-(2-pyrimidyl)piperazin-1-yl}propyl]cis-cyclohex-4-ene-1,2-dicarboximide;
N-[2-hydroxy-3-{4-(2-pyrimidyl)piperazin-1-yl}propyl]cyclohexane-1,2-dicarboximide;
N-[2-acetoxy-3-{4-(2-pyrimidyl)piperazin-1-yl}propyl]cyclohexane-1,2-dicarboximide;
N-[2-isobutyryloxy-3-{4-(2-pyrimidyl)piperazin-1-yl}propyl]cyclohexane-1,2-dicarboximide;
N-[2-cyclohexylcarbonyloxy-3-{4-(2-pyrimidyl)piperazin-1-yl}propyl]cyclohexane-1,2-dicarboximide;
N-[2-hydroxy-3-{4-(2-pyrimidyl)piperazin-1-yl}propyl]endo-bicyclo[2,2,1]hept-5-ene-2,3-dicarboximide;
N-[2-acetoxy-3-{4-(2-pyrimidyl)piperazin-1-yl}propyl]endo-bicyclo[2,2,1]hept-5-ene-2,3-dicarboximide;
N-[2-hydroxy-3-{4-(2-pyrimidyl)piperazin-1-yl}propyl]exo-bicyclo[2,2,1]hept-5-ene-2,3-dicarboximide;
N-[2-hydroxy-3-{4-(2-pyrimidyl)piperazin-1-yl}propyl]phthalimide;
N-[2-benzoyloxy-3-{4-(2-pyrimidyl)piperazin-1-yl}propyl]endo-bicyclo[2,2,1]hept-5-ene-2,3-dicarboximide;
N-[2-n-hexadecanoyloxy-3-{4-(2-pyrimidyl)piperazin-1-yl}propyl]cis-cyclohex-4-ene-1,2-dicarboximide;
N-[3-{4-(2-benzothiazoyl)piperazin-1-yl}-2-hydroxypropyl]endo-bicyclo[2,2,1]hept-5-ene-2,3-dicarboximide;
N-[3-{4-(2-benzothiazoyl)piperazin-1-yl}-2-hydroxypropyl]cis-cyclohex-4-ene-1,2-dicarboximide;
N-[2-benzoyloxy-3-{4-(2-benzothiazoyl)piperazin-1-yl}propyl]cis-cyclohex-4-ene-1,2-dicarboximide;
N-[2-acetoxy-3-{4-(2-benzothiazoyl)piperazin-1-yl}propyl]cyclohexane-1,2-dicarboximide;
N-[2-n-hexadecanoyloxy-3-{4-(2-benzothiazoyl)piperazin-1-yl}propyl]succinimide;
N-{2-hydroxy-3-(4-methylpiperazin-1-yl)propyl}cis-cyclohex-4-ene-1,2-dicarboximide;
N-{2-n-caproyloxy-3-(4-methylpiperazin-1-yl)propyl}cyclohexane-1,2-dicarboximide;
N-{3-(4-methylpiperazin-1-yl)-2-nicotinyloxypropyl}endo-bicyclo[2,2,1]hept-5-ene-2,3-dicarboximide;
N-{2-n-caproyloxy-3-(4-methylpiperazin-1-yl)propyl}endo-bicyclo[2,2,1]hept-5-ene-2,3-dicarboximide;
N-{2-hydroxy-3-(4-methylpiperazin-1-yl)propyl}endo-bicyclo[2,2,1]hept-5-ene-2,3-dicarboximide;
N-{3-(4-methylpiperazin-1-yl)-2-nicotinyloxypropyl}cis-cyclohex-4-ene-1,2-dicarboximide;
N-{2-isobutyryloxy-3-(4-methylpiperazin-1-yl)propyl}cyclohexane-1,2-dicarboximide;
N-{2-n-caproyloxy-3-(4-methylpiperazin-1-yl)propyl}cis-cyclohex-4-ene-1,2-dicarboximide;
N-{2-isobutyryloxy-3-(4-methylpiperazin-1-yl)propyl}cis-cyclohex-4-ene-1,2-dicarboximide;
N-{2-hydroxy-3-(4-methylpiperazin-1-yl)propyl}cyclohexane-1,2-dicarboximide;
N-{2-cyclohexylcarbonyloxy-3-(4-n-hexylpiperazin-1-yl)propyl}cyclohexane-1,2-dicarboximide;
N-{2-cyclohexylcarbonyloxy-3-(4-n-hexylpiperazin-1-yl)propyl}phthalimide;
N-{2-benzoyloxy-3-(4-ethylpiperazin-1-yl)propyl}phthalimide;

N-{2-hexadecanoyloxy-3-(4-propylpiperazin-1-yl)propyl}endo-bicyclo[2,2,2]oct-5-ene-2,3-dicarboximide;
N-{2-benzoyloxy-3-(4-n-hexylpiperazin-1-yl)propyl} cis-cyclohex-4-ene-1,2-dicarboximide;
N-{2-hydroxy-3-(4-phenylpiperazin-1-yl)propyl}exo-bicyclo[2,2,1]hept-5-ene-2,3-dicarboximide;
N-[2-acetoxy-3-{4-(3-chlorophenyl)piperazin-1-yl}propyl]phthalimide;
N-[2-acetoxy-3-{4-(3-chlorophenyl)piperazin-1-yl}propyl]cyclohexane-1,2-dicarboximide;
N-[2-acetoxy-3-{4-(3-chlorophenyl)piperazin-1-yl}propyl]cis-cyclohex-4-ene-1,2-dicarboximide;
N-[2-acetoxy-3-{4-(3-chlorophenyl)piperazin-1-yl}propyl]exo-bicyclo[2,2,1]hept-5-ene-2,3-dicarboximide;
N-[2-benzoyloxy-3-{4-(3-chlorophenyl)piperazin-1-yl}propyl]endo-bicyclo[2,2,1]hept-5-ene-2,3-dicarboximide;
N-[2-n-caproyloxy-3-{4-(3-chlorophenyl)piperazin-1-yl}propyl]endo-bicyclo[2,2,1]hept-5-ene-2,3-dicarboximide;
N-[2-acetoxy-3-{4-(3-chlorophenyl)piperazin-1-yl}propyl]endo-bicyclo[2,2,1]hept-5-ene-2,3-dicarboximide;
N-[3-{4-(3-chlorophenyl)piperazin-1-yl}-2-hydroxypropyl]exo-bicyclo[2,2,1]hept-5-ene-2,3-dicarboximide;
N-[2-hydroxy-3-{4-(2-methoxyphenyl)piperazin-1-yl}propyl]exo-bicyclo[2,2,1]hept-5-ene-2,3-dicarboximide;
N-[3-{4-(3-chlorophenyl)piperazin-1-yl}-2-hydroxypropyl]exo-bicyclo[2,2,1]heptane-2,3-dicarboximide;
N-[3-{4-(3-chlorophenyl)piperazin-1-yl}-2-hydroxypropyl]endo-bicyclo[2,2,1]hept-5-ene-2,3-dicarboximide;
N-[2-cyclohexylcarbonyloxy-3-{4-(4-methylphenyl)piperazin-1-yl}propyl]endo-bicyclo[2,2,1]hept-5-ene-2,3-dicarboximide;
N-[2-hexadecanoyloxy-3-{4-(3-trifluoromethylphenyl)piperazin-1-yl}propyl]endo-7-oxabicyclo[2,2,1]heptane-2,3-dicarboximide;
N-[2-cyclohexylcarbonyloxy-3-{4-phenylpiperazin-1-yl}propyl]cis-cyclohex-4-ene-1,2-dicarboximide;
N-[2-cyclohexylcarbonyloxy-3-{4-(3,4-dimethylphenyl)piperazin-1-yl}propyl]endo-bicyclo[2,2,2]oct-5-ene-2,3-dicarboximide;
N-[2-benzoyloxy-3-{4-(2-methoxyphenyl)piperazin-1-yl}propyl]phthalimide;
N-[2-n-hexadecanoyloxy-3-{4-(4-chlorophenyl)piperazin-1-yl}propyl]endo-bicyclo[2,2,1]hept-5-ene-2,3-dicarboximide,
N-[3-{4-<2-(4,6-dimethyl)pyrimidyl>piperazin-1-yl}-2-hydroxypropyl]cis-cyclohex-4-ene-1,2-dicarboximide;
N-[3-{4-<2-(4,6-dimethyl)pyrimidyl>piperazin-1-yl}-2-hydroxypropyl]endo-bicyclo[2,2,1]hept-5-ene-2,3-dicarboximide;
N-[2-n-hexanoyloxy-3-{4-<2-(4,6-dimethyl)pyrimidyl>piperazin-1-yl}propyl]cis-cyclohex-4-ene-1,2-dicarboximide;
N-[2-cyclohexylcarbonyloxy-3-{4-<2-(4-methoxy-6-methyl)pyrimidyl>piperazin-1-yl}propyl]endo-bicyclo[2,2,1]hept-5-ene-2,3-dicarboximide;
N-[2-hexanoyloxy-3-{4-<2-(3-methyl)pyridyl>piperazin-1-yl}propyl]cis-cyclohex-4-ene-1,2-dicarboximide;
N-[2-cyclohexylcarbonyloxy-3-{4-(4-pyridyl)piperazin-1-yl}propyl]endo-bicyclo[2,2,1]hept-5-ene-2,3-dicarboximide;
N-[2-propanoyloxy-3-{4-<2-(4-methoxy)pyridyl>piperazin-1-yl}propyl]phthalimide;
N-[2-propanoyloxy-3-{4-<2-(4-chloro)pyridyl>piperazin-1-yl}propyl]phthalimide;
N-[2-cyclohexylcarbonyloxy-3-{4-(4-pyridyl)piperazin-1-yl}propyl]succinimide;
N-[2-hydroxy-3-{4-(2-pyrimidyl)hexahydro-1H-1,4-diazepin-1-yl}propyl]cis-cyclohex-4-ene-1,2-dicarboximide;
N-[2-hydroxy-3-{4-(2-pyrimidyl)hexahydro-1H-1,4-diazepin-1-yl}propyl]endo-bicyclo[2,2,1]hept-5-ene-2,3-dicarboximide;
N-[2-hydroxy-3-{4-(2-pyridyl)hexahydro-1H-1,4-diazepin-1-yl}propyl]cis-cyclohex-4-ene-1,2-dicarboximide;
N-[2-hydroxy-3-{4-(2-pyridyl)hexahydro-1H-1,4-diazepin-1-yl}propyl]endo-bicyclo[2,2,1]hept-5-ene-2,3-dicarboximide;
N-[2-n-caproyloxy-3-{4-(2-pyridyl)hexahydro-1H-1,4-diazepin-1-yl}propyl]cis-cyclohex-4-ene-1,2-dicarboximide;
N-{2-hydroxy-3-(4-phenylhexahydro-1H-1,4-diazepin-1-yl)propyl}cis-cyclohex-4-ene-1,2-dicarboximide;
N-{2-hydroxy-3-(4-phenylhexahydro-1H-1,4-diazepin-1-yl)propyl}endo-bicyclo[2,2,1]hept-5-ene-2,3-dicarboximide;
N-[2-n-caproyloxy-3-{4-(2-pyridyl)hexahydro-1H-1,4-diazepin-1-yl}propyl]endo-bicyclo[2,2,1]hept-5-ene-2,3-dicarboximide;
N-[2-cyclohexylcarbonyloxy-3-{4-methyl-hexahydro-1H-1,4-diazepin-1-yl}propyl]phthalimide;
N-[2-cyclohexylcarbonyloxy-3-{4-phenyl-hexahydro-1H-1,4-diazepin-1-yl}propyl]succinimide;
N-[2-nicotinoyloxy-3-{4-(3,4-dimethylphenyl)-hexahydro-1H-1,4-diazepin-1-yl}propyl]cyclohexane-1,2-dicarboximide;
N-[2-cyclohexylcarbonyloxy-3-{4-<2-(4,6-dimethyl)pyrimidyl>-hexahydro-1H-1,4-diazepin-1-yl}propyl]endo-bicyclo[2,2,1]hept-5-ene-2,3-dicarboximide;
N-[2-n-butylaminocarbonyloxy-3-{4-ethyl-hexahydro-1H-1,4-diazepin-1-yl}propyl]exo-bicyclo[2,2,1]hept-5-ene-2,3-dicarboximide;
N-[2-n-hexadecanoyloxy-3-{4-(2-pyridyl)hexahydro-1H-1,4-diazepin-1-yl}propyl]cis-cyclohex-4-ene-1,2-dicarboximide;
N-[2-(2-benzylcarbonyloxy)-3-{4-(2-pyridyl)hexahydro-1H-1,4-diazepin-1-yl}propyl]cis-cyclohex-4-ene-1,2-dicarboximide;
2-[2-hydroxy-3-{4-(2-pyridyl)piperazin-1-yl}propyl]-1H-benz[d,e]isoquinoline-1,3(2H)dione;
2-[2-n-caproyloxy-3-{4-(2-pyridyl)piperazin-1-yl}propyl]-1H-benz[d,e]isoquinoline-1,3(2H)dione;
2-[2-cyclohexylcarbonyloxy-3-{4-(2-pyridyl)piperazin-1-yl}propyl]-1H-benz[d,e]isoquinoline-1,3(2H)dione;
N-{2-hydroxy-3-(4-phenylpiperazin-1-yl)propyl}cis-cyclohex-4-ene-1,2-dicarboximide;
N-[2-hydroxy-3-{4-(2-methylphenyl)piperazin-1-yl}propyl]endo-bicyclo[2,2,1]hept-5-ene-2,3-dicarboximide;
N-[3-{4-<2-(4,6-dimethyl)pyrimidyl>piperazin-1-yl}-2-hydroxypropyl]phthalimide;
N-[2-n-caproyloxy-3{4-<2-(4,6-dimethyl)pyrimidyl>piperazin-1-yl}propyl]phthalimide;

N-[2-cyclohexylcarbonyloxy-3-{4-(2-methylphenyl)-piperazin-1-yl}propyl]endo-bicyclo[2,2,1]hept-5-ene-2,3-dicarboximide;

N-{2-cyclohexylcarbonyloxy-3-(4-phenylpiperazin-1-yl)propyl}cis-cyclohex-4-ene-1,2-dicarboximide;

N-[2-hydroxy-3-{4-(2-pyridyl)piperazin-1-yl}propyl]2,2-dimethylsuccinimide;

N-[2-cyclohexylcarbonyloxy-3-{4-(2-pyridyl)piperazin-1-yl}propyl]2,2-dimethylsuccinimide;

N-[2-n-caproyloxy-3-{4-(2-pyridyl)piperazin-1-yl}propyl]2,2-dimethylsuccinimide.

In order to explain the effect of the present invention in more detail, experimental examples on hypoglycemic activity are given below.

EXPERIMENT 1

Improvement of glucose tolerance

Male Sprague-Dawley rats (weighing 300–350 g) were maintained on rat chow and water adlibitum in a constant temperature room (22°–24° C.) for at least a week prior to use in studies. Sub-diabetic rats*[1] were obtained by intrevenous injection of 20 mg/kg of streptozotocin (STZ). The compounds were orally administered in 5% gum arabic suspension in sub-diabetic rats. 3 g/kg of glucose was administered intraperitoneally an hour later. Blood samples were taken from the tail vein, and the blood sugar was measured by the anthrone method [Ui. M., Am. J. Physiol. 209, 353–358 (1965)]. The results are shown in Table 1, in which the numerical values are the improvement percentages of the blood sugar value of each group treated with compounds relative to those of the control group expressed as 100%.

*[1]: STZ sub-diabetic rats are obtained by administering a low dose of streptozotocin (20 mg/kg) dissolved in physiological saline containing 1 mM citrate buffer (pH 4.5) into the superficial cutaneous vein. These animals exhibit sub-diabetic conditions such that the blood sugar value on feeding is 100–130 mg/dl but show impaired response to administered glucose.

Names of Test Compounds

Compound A: N-[2-Cyclohexylcarbonyloxy-3-{4-(2-pyridyl)piperazin-1-yl}propyl]succinimide maleate;

Compound B: N-[2-n-Decanoyloxy-3-{4-(2-pyridyl)-piperazin-1-yl}propyl]cis-cyclohex-4-ene-1,2-dicarboximide dimaleater;

Compound C: N-[2-n-Caproyloxy-3-{4-(2-pyridyl)piperazin-1-yl}propyl]cis-cyclohex-4-ene-1,2-dicarboximide dimaleate;

Compound D: N-[2-(trans-2-Nonenoyloxy)-3-{4-(2-pyridyl)piperazin-1-yl}propyl]cis-cyclohex-4-ene-1,2-dicarboximide dimaleate;

Compound E: N-[2-Nicotinoyloxy-3-{4-(2-pyridyl)piperazin-1-yl}propyl]cis-cyclohex-4-ene-1,2-dicarboximide maleate Compound F: N-[2-Cyclohexylcarbonyloxy-3-{4-(2-pyridyl)piperazin-1-yl}propyl]endo-cis-bicyclo[2,2,1-]hept-5-ene-2,3-dicarboximide dimaleate;

Compound G: N-[2-Palmitoyloxy-3-{4-(2-pyridyl)piperazin-1-yl}propyl]cis-cyclohex-4-ene-1,2-dicarboximide dimaleate;

Compound H: N-[2-Nicotinoyloxy-3-{4-(2-pyridyl)piperazin-1-yl}propyl]phthalimide maleate;

Compound I: N-[2-Propionyloxy-3-{4-(2-pyridyl)piperazin-1-yl}propyl]phthalimide maleate; and Compound J: N-{2-n-Caproyloxy-3-(4-methylpiperazin-1-yl)propyl}cis-cyclohex-4-ene-1,2-dicarboximide dimaleate.

TABLE 1

| Test Compound | No. of Animals | Dosage (mg/kg) | Improvement percent of glucose tolerance (%)*[2] | | |
|---|---|---|---|---|---|
| | | | 1 hr. | 2 hrs. | 3 hrs. |
| Compound A | 4 | 10 | 12 | 25 | 19 |
| Compound B | 4 | 10 | 15 | 23 | 26 |
| Compound C | 7 | 10 | 7 | 17 | 23 |
| Compound D | 4 | 10 | 0 | 13 | 26 |
| Compound E | 4 | 10 | 11 | 20 | 9 |
| Compound F | 8 | 10 | 14 | 25 | 34 |
| Compound G | 4 | 10 | 3 | 15 | 24 |
| Compound H | 4 | 10 | 19 | 23 | 27 |
| Compound I | 6 | 10 | 14 | 26 | 31 |
| Compound J | 5 | 10 | 0 | 21 | 32 |

*[2]The improvement percent of glucose tolerance means a percentage of blood sugar of the group treated with the test compounds each after glucose load (1, 2 and 3 hours after) relative to that of the control group expressed as 100%.

From Table 1 it can be seen that the compounds of the present invention obviously possess extremely excellent improvement ability of glucose tolerance and therefore they are useful as agents for diabetes.

For toxicity of the compounds of the present invention, they are extremely safe drugs as demonstrated by the following experiment.

More specifically, when an experiment was carried out in DDY strain mice, there was no case of death at a dosage of 1,000 mg/kg, as shown below.

EXPERIMENT 2

Acute Toxicity Test

DDY strain mice (weighing 20–25 g) maintained on mice chow and water adlibitum in a constant temperature room (22°–24° C.) for at least a week were used.

An acute toxicity test was carried out by oral administration of the compounds at two dosage levels of 500 mg/kg and 1,000 mg/kg. Observation of dead cases were made within one week. In table 2, the denominator of each value indicates the number of cases tested and the numerator indicates the number of dead cases. Compounds A, B, C, D, E and F correspond to Compoounds A–F in Experiment 1 respectively.

TABLE 2

| Test Compound | Acute Toxicity | |
|---|---|---|
| | 500 mg/kg | 1,000 mg/kg |
| Compound A | 0/5 | 0/5 |
| Compound B | 0/5 | 0/5 |
| Compound C | 0/5 | 0/5 |
| Compound D | 0/5 | 0/5 |
| Compound E | 0/5 | 0/5 |
| Compound F | 0/5 | 0/5 |

When the compounds of the present invention are used as agents for diabetes, they are administered either orally or parenterally (e.g. intramuscularly, subcutaneously, intravenously, as suppositories etc.). Although the dosage depends on the severity of the condition of the patient, it is generally in the range of 100–1,000 mg, preferably 250–500 mg, per day for a human adult.

For preparations of the compounds of the present invention, they are made in the form of tablets, granules, powders, capsules, injectable compositions, suppositories etc. in accordance with conventional pharmaceutical practice.

More specifically, for preparing oral solid preparations, the main drug is mixed with an excipient and further, if necessary, a binder, disintegrantor, lubricant, cooling agent, flavoring agent etc. and made into tablets, coated tablets, granules, powders, capsules etc. in conventional manner.

As the excipients, there can be used, for example, lactose, corn starch, white sugar, glucose, sorbitol, microcrystalline cellulose etc. As the binders, there can be used, for example, polyvinyl alcohol, polyvinyl ether, ethyl cellulose, methyl cellulose, gum arabic, tragacanth, gelatin, shellac, hydroxypropyl cellulose, hydroxypropyl starch, polyvinylpyrrolidone etc. As the disintegrantors, there can be used, for example starch, agar, gelatin powder, microcrystalline cellulose, calcium carbonate, sodium bicarbonate, calcium citrate, dextrin, pectin etc. As the lubricants, there can be used, for example, magnesium stearate, talc, polyethylene glycol, silica, hardened vegetable oils etc. As the colorants, there can be used those allowed as additives to medicine such as cocoa butter, menthol, aromatic acids, mint oil, camphol, cinnamon powder etc. These tablets, granules etc. may of course be suitably coated with sugar, gelatin or the like, if necessary.

For preparing injectable solution, the main drug is mixed with a pH adjusting agent, buffer, stabilizer, preservative etc., if necessary, and made into compositions for subcutaneous, intramuscular, intravenous injections etc. in conventional manner.

EXAMPLE 1

N-[2-Hydroxy-3-{4-(2-pyridyl)piperazin-1-yl}propyl]-endo-cis-bicyclo[2,2,1]hept-5-ene-2,3-dicarboximide (1) Synthesis of N-(2,3-epoxypropyl)endo-cis-bicyclo[2,2,1]hept-5-ene-2,3-dicarboximide One liter of 2-butanone was added to 65.2 g of endo-cis-bicyclo[2,2,1]hept-5-ene-2,3-dicarboximide, 70 g of epichlorohydrin and anhydrous potassium carbonate, and the mixture was heated under reflux for 5 hours. The inorganic matters were filtered while hot, the filtrate was concentrated, and the separated crystals were filtered to obtain 70.9 g of the title compound, yield 81%, m.p. 112°–114° C.

| Elemental analysis: for $C_{12}H_{13}NO_3$ | | | |
|---|---|---|---|
| | C | H | N |
| Calculated (%): | 65.74 | 5.98 | 6.39 |
| Found (%): | 66.01 | 5.79 | 6.43 |

(2) Synthesis of N-[2-hydroxy-3-{4-(2-pyridyl)piperazin-1-yl}propyl]-endo-cis-bicyclo[2,2,1]hept-5-ene-2,3-dicarboximide 200 ml of ethanol was added to 10.95 g of the N-(2,3-epoxypropyl)endo-cis-bicyclo[2,2,1]hept-5-ene-2,3-dicarboximide obtained by the process (1) and 8.2 g of 1-(2-pyridyl)piperazine, and the mixture was heated under reflux for 3 hours. The desired compound separated on standing to cool, and this was filtered to obtain 17.8 g (yield 93%) of the title compound.

Melting point: 142°–144° C.

| Elemental analysis: for $C_{21}H_{20}N_4O_3$ | | | |
|---|---|---|---|
| | C | H | N |
| Calculated (%): | 65.95 | 6.85 | 14.65 |
| Found (%) | 66.05 | 6.93 | 14.47 |

EXAMPLE 2

N-[2-Acetoxy-3-{4-(2-pyridyl)piperazin-1-yl}propyl]-cis-cyclohex-4-ene-1,2-dicarboximide dimaleate 2.2 g of N-[2-hydroxy-3-{4-(2-pyridyl)piperazin-1-yl}propyl]cis-cyclohex-4-ene-1,2-dicarboximde was dissolved in 1,2-dichloroethane, and 0.8 g of acetyl chloride was added to the solution, which was then heated under reflux for about 30 minutes. Thereafter, this was cooled to 0° C., a 5% aqueous sodium carbonate solution was added to adjust the pH to 9, and the organic layer was separated. This was washed with water and dried over anhydrous magnesium sulfate, followed by filtration. The filtrate was concentrated. Then, ethyl acetate was added to the residue to dissolve. Then, a solution of 0.69 g of maleic acid dissolved in a mixed solvent of ethyl acetate and methanol was added to the solution, which was then heated under reflux for 5 minutes. The desired compound separated on standing to cool, and this was filtered to obtain 2.9 g (yield 93%) of the title compound.

Melting point: 144°–147° C.

| Elemental analysis: for $C_{22}H_{28}N_4O_4.2C_4H_4O_4$ | | | |
|---|---|---|---|
| | C | H | N |
| Calculated (%): | 55.89 | 5.64 | 8.69 |
| Found (%) | 55.67 | 5.75 | 8.56 |

EXAMPLE 3

N-[2-n-Decanoyloxy-3-{4-(2-pyridyl)piperazin-1-yl}propyl]cis-cyclohexane-1,2-dicarboximide dimaleate 1.86 g of N-[2-hydroxy-3-{4-(2-pyridyl)piperazin-1-yl}propyl]cis-cyclohexane-1,2-dicarboximide was dissolved in 50 ml of 1,2-dichloroethane, and 1.2 g of n-decanoyl chloride was added to this solution, which was heated under reflux for an hour. Thereafter, 1,2-dichloroethane was distilled off under reduced pressure, ether and dilute hydrochloric acid were added with ice cooling and the mixture was stirred. The aqueous layer was separated, adjusted to pH 9 by adding a 5% aqueous sodium carbonate solution with ice cooling, and extracted with chloroform. The extract was washed with water and then dried over anhydrous magnesium sulfate. This was filtered, and the filtrate was concentrated, after which ethyl acetate was added to the residue to dissolve, and a solution of 1.16 g of maleic acid dissolved in a mixed solvent of ethyl acetate and methanol was added to the solution, which was then heated under reflux for 5 minutes. The desired compound separated on standing to cool, and this was filtered to obtain 3.4 g (yield 90%) of the title compound.

Melting point: 125°–128° C.

| Elemental analysis: for $C_{30}H_{46}N_4O_4.2C_4H_4O_4$ | | | |
|---|---|---|---|
| | C | H | N |
| Calculated (%): | 60.13 | 7.19 | 7.38 |
| Found (%): | 59.84 | 7.09 | 7.36 |

EXAMPLE 4

N-{3-(4-Methylpiperazin-1-yl)-2-nicotinyloxypropyl} cis-cyclohex-4-ene-1,2-dicarboximide dimaleate 1.84 g of N-{2-hydroxy-3-(4-methylpiperazin-1-yl)propyl}cis-cyclohex-4-ene-1,2-dicarboximide and 2.6 g of triethylamine were dissolved in 50 ml of 1,2-dichloroethane, and 1.4 g of nicotinyl chloride hydrochloride was added to this solution, which was heated under reflux for 2 hours. After cooling to 0° C., water was added, the mixture was stirred, and then the organic layer was separated. This was washed with water, and then dried over anhydrous magnesium sulfate. This was filtered, the filtrate was concentrated, 1.4 g of maleic acid and ethanol were added to the residue, and the mixture was heated under reflux for 5 minutes. The desired compound separated on standing to cool, and this was filtered to obtain 3.5 g (yield 91%) of the title compound.

Melting point: 165° C. (dec.)

| Elemental analysis: for $C_{22}H_{28}N_3H_4.2C_4H_4O_4$ | | | |
|---|---|---|---|
| | C | H | N |
| Calculated (%): | 55.89 | 5.64 | 8.69 |
| Found (%): | 55.75 | 5.64 | 8.71 |

EXAMPLE 5

N-[2-n-Butylaminocarbonyloxy-3-{4-(2-pyridyl)piperazin-1-yl}propyl]endo-cis-bicyclo[2,2,1]hept-5-ene-2,3-dicarboximide dimaleate 25 ml of toluene was added to 1.9 g of N-[2-hydroxy-3-{4-(2-pyridyl)piperazin-1-yl}propyl]endo-cis-bicyclo[2,2,1]hept-5-ene-2,3-dicarboximide, 1.5 g of n-butyl isocyanate and 1 ml of pyridine, and heated at 160° C. using a sealed tube for 6 hours. The solvent was distilled off under reduced pressure, and the residue was dissolved in ethyl acetate, after which a solution of 1.16 g of maleic acid dissolved in a mixed solvent of ethyl acetate-methanol was added to the resulting solution, and heated under reflux for 5 minutes. The desired compound separated on standing to cool, and this was filtered to obtain 3.1 g (yield 87%) of the title compound.

Melting point: 144°-146° C.

| Elemental analysis: for $C_{26}H_{35}N_5O_4.2C_4H_4O_4$ | | | |
|---|---|---|---|
| | C | H | N |
| Calculated (%): | 57.21 | 6.08 | 9.81 |
| Found (%): | 57.28 | 6.03 | 9.85 |

EXAMPLE 6

N-[2-Cyclohexylaminocarbonyloxy-3-{4-(2-pyridyl)-piperazin-1-yl}propyl]cis-cyclohex-4-ene-1,2-dicarboximide dimaleate 25 ml of xylene was added to 1.85 g of N-[2-hydroxy-3-{4-(2-pyridyl)piperazin-1-yl}propyl]cis-cyclohex-4-ene-1,2-dicarboximide and 2 g of cyclohexyl isocyanate, and heated at 180° C. using a sealed tube for 8 hours. The xylene was distilled off under reduced pressure, and the residue was then dissolved in ethyl acetate, after which a solution of 1.16 g of maleic acid dissolved in a mixed solvent of ethyl acetate and methanol was added to this solution, and heated under reflux for 5 minutes. The desired compound separated on standing to cool, and this was filtered to obtain 3.2 g (yield 88%) of the title compound.

Melting point: 151°-153° C.

| Elemental analysis: for $C_{27}H_{37}N_5O_4.2C_4H_4O_4$ | | | |
|---|---|---|---|
| | C | H | N |
| Calculated (%): | 57.75 | 6.24 | 9.62 |
| Found (%): | 57.66 | 6.19 | 9.55 |

EXAMPLE 7

N-[2-Cyclohexylcarbonyloxy-3-{4-(2-pyridyl)piperazin-1-yl}propyl]-endo-cis-bicyclo[2,2,1]hept-5-ene-2,3-dicarboximide dihydrochloride 3.82 g of N-[2-hydroxy-3-{4-(2-pyridyl)piperazin-1-yl}propyl]-endo-cis-bicyclo[2,2,1]hept-5-ene-2,3-dicarboximide was dissolved in 100 ml of 1,2-dichloroethane. To the solution was added 1.8 g of cyclohexanecarbonyl chloride. The whole was heated under reflux for 5 hours. The 1,2-dichloroethane was distilled off under reduced pressure. To the residue was added under ice-cooling a mixture of ether and diluted hydrochloric acid. The whole was stirred. The aqueous layer was recovered by separation. To the recovered solution was added under ice-cooling 5% aqueous sodium hydroxide solution, thereby making its pH to 10. The mixture was extracted with chloroform. The extract was washed with water, followed by dried over anhydrous magnesium sulfate. It was filtered, the filtrate was concentrated, the residue was recrystallized from ethanol to obtain 4.4 g of free amine compound, that is, N-[2-cyclohexylcarbonyloxy-3-{4-(2-pyridyl)piperazin-1-yl}propyl]endo-cis-bicyclo[2,2,1]hept-5-ene-2,3-dicarboxamide (melting point: 149°-151° C.). The resulting crystalline mass was dissolved in ethanol while hot. To the solution was added a solution which was previously prepared by diluting 2 g of concentrated hydrochloric acid with 100 ml of ethanol. The desired compound separated on standing to cool, and this was filtered to obtain 4.8 g (yield 85%) of the title compound.

Melting point: 241°-243° C. (dec.)

| Elemental analysis: for $C_{28}H_{36}N_4O_4.2HCl$ | | | |
|---|---|---|---|
| | C | H | N |
| Calculated (%): | 59.46 | 6.79 | 9.91 |
| Found (%): | 59.31 | 6.81 | 9.90 |

The above-mentioned compound was administered to 6 rats in a dosage of 39 mg/kg. The experimental method was carried out in a similar manner as described in Experiment 1. Improvement percent of glucose tolerance was thus obtained at 23% after 1 hour; 33% after 2 hours; and 37% after 3 hours, respectively.

The following compounds were obtained by procedures similar to those in Example 1.

N-[2-Hydroxy-3-{4-(2-pyridyl)piperazin-1-yl}propyl]-cis-cyclohex-4-ene-1,2-dicarboximide fumarate Melting point: 170°-172° C.

| Elemental analysis: for $C_{20}H_{26}N_4O_3.C_4H_4O_4$ | | | |
|---|---|---|---|
| | C | H | N |
| Calculated (%): | 59.25 | 6.22 | 11.52 |

-continued

Elemental analysis: for $C_{20}H_{26}N_4O_3 \cdot C_4H_4O_4$

| | C | H | N |
|---|---|---|---|
| Found (%): | 59.39 | 6.20 | 11.47 |

N-[2-Hydroxy-3-{4-(2-pyridyl)piperazin-1-yl}propyl]-cis-cyclohexane-1,2-dicarboximide maleate
Melting point: 159°–161° C.

Elemental analysis: for $C_{20}H_{28}N_4O_3 \cdot C_4H_4O_4$

| | C | H | N |
|---|---|---|---|
| Calculated (%): | 59.00 | 6.60 | 11.47 |
| Found (%): | 59.13 | 6.56 | 11.55 |

N-[2-Hydroxy-3-{4-(2-pyridyl)piperazin-1-yl}propyl]-succinimide dimaleate
Melting point: 146°–148° C.

Elemental analysis: for $C_{16}H_{22}N_4O_3 \cdot 2C_4H_4O_4$

| | C | H | N |
|---|---|---|---|
| Calculated (%): | 52.35 | 5.50 | 10.18 |
| Found (%): | 52.46 | 5.53 | 10.14 |

N-[2-Hydroxy-3-{4-(2-pyridyl)piperazin-1-yl}propyl]exo-cis-bicyclo[2,2,1]hept-5-ene-2,3-dicarboximide
Melting point: 191°–192° C.

Elemental analysis: for $C_{21}H_{26}N_4O_3$

| | C | H | N |
|---|---|---|---|
| Calculated (%): | 65.95 | 6.85 | 14.65 |
| Found (%): | 65.75 | 6.90 | 14.80 |

N-[2-Hydroxy-3-{4-(2-pyridyl)piperazin-1-yl}propyl]phthalimide
Melting point: 147°–149° C.

Elemental analysis: for $C_{20}H_{22}N_4O_3$

| | C | H | N |
|---|---|---|---|
| Calculated (%): | 65.55 | 6.05 | 15.29 |
| Found (%): | 65.84 | 6.20 | 15.41 |

N-[2-Hydroxy-3-{4-(2-pyridyl)piperazin-1-yl}propyl]endo-cis-bicyclo[2,2,2]oct-5-ene-2,3-dicarboximide
Melting point: 156°–158° C.

Elemental analysis: for $C_{22}H_{28}N_4O_3$

| | C | H | N |
|---|---|---|---|
| Calculated (%): | 66.64 | 7.12 | 14.13 |
| Found (%): | 66.63 | 7.08 | 13.98 |

N-[2-Hydroxy-3-{4-(2-pyridyl)piperazin-1-yl}propyl]endo-cis-bicyclo[2,2,1]heptane-2,3-dicarboximide
Melting point: 156°–158° C.

Elemental analysis: for $C_{21}H_{28}N_4O_3$

| | C | H | N |
|---|---|---|---|
| Calculated (%): | 65.60 | 7.34 | 14.57 |
| Found (%): | 65.90 | 7.39 | 14.60 |

N-[2-Hydroxy-3-{4-(2-pyridyl)piperazin-1-yl}propyl]endo-cis-7-oxabicyclo[2,2,1]heptane-2,3-dicarboximide maleate
Melting point: 179°–181° C.

Elemental analysis: for $C_{20}H_{26}N_4O_4 \cdot C_4H_4O_4$

| | C | H | N |
|---|---|---|---|
| Calculated (%): | 57.35 | 6.02 | 11.15 |
| Found (%): | 57.26 | 5.99 | 11.16 |

N-{2-Hydroxy-3-(4-phenylhexahydro-1H-1,4-diazepin-1-yl)propyl}cis-cyclohex-4-ene-1,2-dicarboximide
Melting point: 134°–136° C.

Elemental analysis: for $C_{22}H_{29}N_3O_3$

| | C | H | N |
|---|---|---|---|
| Calculated (%): | 68.90 | 7.62 | 10.96 |
| Found (%): | 68.76 | 7.69 | 10.78 |

N-[2-Hydroxy-3-{4-(2-pyrimidyl)piperazin-1-yl}propyl]cis-cyclohex-4-ene-1,2-dicarboximide maleate
Melting point: 172° C. (dec.)

Elemental analysis: for $C_{19}H_{25}N_5O_3 \cdot C_4H_4O_4$

| | C | H | N |
|---|---|---|---|
| Calculated (%): | 56.65 | 6.01 | 14.37 |
| Found (%): | 56.48 | 6.00 | 14.25 |

N-[2-Hydroxy-3-{4-(2-pyrimidyl)piperazin-1-yl}propyl]cis-cyclohexane-1,2-dicarboximide maleate
Melting point: 191° C. (dec.)

Elemental analysis: for $C_{19}H_{27}N_5O_3 \cdot C_4H_4O_4$

| | C | H | N |
|---|---|---|---|
| Calculated (%): | 56.42 | 6.40 | 14.31 |
| Found (%): | 56.27 | 6.35 | 14.29 |

N-[2-Hydroxy-3-{4-(2-pyrimidyl)piperazin-1-yl}propyl]endo-cis-bicyclo[2,2,1]hept-5-ene-2,3-dicarboximide
Melting point: 147°–150° C.

Elemental analysis: for $C_{20}H_{25}N_5O_3$

| | C | H | N |
|---|---|---|---|
| Calculated (%): | 62.64 | 6.57 | 18.27 |
| Found (%): | 62.73 | 6.59 | 18 23 |

N-[2-Hydroxy-3-{4-(2-pyrimidyl)piperazin-1-yl}propyl]exo-cis-bicyclo[2,2,1]hept-5-ene-2,3-dicarboximide
Melting point: 180°–182° C.

Elemental analysis: for $C_{20}H_{25}N_5O_3$

| | C | H | N |
|---|---|---|---|
| Calculated (%): | 62.64 | 6.57 | 18.27 |
| Found (%): | 62.39 | 6.54 | 18.32 |

N-[2-Hydroxy-3-{4-(2-pyrimidyl)piperazin-1-yl}propyl]phthalimide
Melting point: 114°–118° C.

| Elemental analysis: for $C_{19}H_{21}N_5O_3$ | | | |
|---|---|---|---|
| | C | H | N |
| Calculated (%): | 62.11 | 5.76 | 19.06 |
| Found (%): | 61.91 | 5.53 | 18.92 |

N-[3-{4-(2-benzothiazoyl)piperazin-1-yl}-2-hydroxypropyl]endo-cis-bicyclo[2,2,2]hept-5-ene-2,3-dicarboximide
Melting point: 160°–163° C.

| Elemental analysis: for $C_{23}H_{26}N_4O_3S$ | | | |
|---|---|---|---|
| | C | H | N |
| Calculated (%): | 62.98 | 5.99 | 12.78 |
| Found (%): | 62.75 | 5.77 | 12.57 |

N-[3-{4-<2-(4,6-Dimethyl)pyrimidyl>piperazin-1-yl}-2-hydroxypropyl]endo-cis-bicyclo[2,2,1]hept-5-ene-2,3-dicarboximide
Melting point: 135°–137° C.

| Elemental analysis: for $C_{22}H_{29}N_5O_3$ | | | |
|---|---|---|---|
| | C | H | N |
| Calculated (%): | 64.21 | 7.10 | 17.02 |
| Found (%): | 64.10 | 7.16 | 17.08 |

N-[3-{4-(3-Chlorophenyl)piperazin-1-yl}-2-hydroxypropyl]endo-cis-bicyclo[2,2,1]hept-5-ene-2,3-dicarboximide
Melting point: 134°–135° C.

| Elemental analysis: for $C_{22}H_{26}N_3ClO_3$ | | | |
|---|---|---|---|
| | C | H | N |
| Calculated (%): | 63.52 | 6.31 | 10.10 |
| Found (%): | 63.74 | 6.30 | 10.18 |

N-[3-{4-(2-Benzothiazolyl)piperazin-1-yl}-2-hydroxypropyl]cis-cyclohex-4-ene-1,2-dicarboximide maleate
Melting point: 177° C. (dec.)

| Elemental analysis: for $C_{22}H_{26}N_4O_3S \cdot C_4H_4O_4$ | | | |
|---|---|---|---|
| | C | H | N |
| Calculated (%): | 57.54 | 5.58 | 10.33 |
| Found (%): | 57.70 | 5.65 | 10.21 |

N-[3-{4-<2-(4,6-Dimethyl)pyrimidyl>piperazin-1-yl}-2-hydroxypropyl]cis-cyclohex-4-ene-1,2-dicarboximide maleate
Melting point: 157°–159° C.

| Elemental analysis: for $C_{21}H_{29}N_5O_3 \cdot C_4H_4O_4$ | | | |
|---|---|---|---|
| | C | H | N |
| Calculated (%): | 58.23 | 6.46 | 13.59 |
| Found (%): | 58.11 | 6.51 | 13.40 |

N-[3-{4-(3-Chlorophenyl)piperazin-1-yl}-2-hydroxypropyl]exo-cis-bicyclo[2,2,1]heptane-2,3-dicarboximide
Melting point: 154°–156° C.

| Elemental analysis: for $C_{22}H_{28}ClN_3O_3$ | | | |
|---|---|---|---|
| | C | H | N |
| Calculated (%): | 63.21 | 6.77 | 10.06 |
| Found (%): | 63.36 | 6.84 | 10.03 |

N-{2-Hydroxy-3-(4-phenylpiperazin-1-yl)propyl}exo-cis-bicyclo[2,2,1]hept-5-ene-2,3-dicarboximide maleate
Melting point: 179°–180° C.

| Elemental analysis: for $C_{22}H_{27}N_3O_3 \cdot C_4H_4O_4$ | | | |
|---|---|---|---|
| | C | H | N |
| Calculated (%): | 62.75 | 6.29 | 8.45 |
| Found (%): | 62.67 | 6.28 | 8.32 |

N-[3-{4-(3-Chlorophenyl)piperazin-1-yl}-2-hydroxypropyl]exo-cis-bicyclo[2,2,1]hept-5-ene-2,3-dicarboxamide
Melting point: 152°–154° C.

| Elemental analysis: for $C_{22}H_{26}ClN_3O_3$ | | | |
|---|---|---|---|
| | C | H | N |
| Calculated (%): | 63.52 | 6.31 | 10.10 |
| Found (%): | 63.37 | 6.39 | 9.95 |

N-[2-Hydroxy-3-{4-(2-methoxyphenyl)piperazin-1-yl}propyl]exo-cis-bicyclo[2,2,1]hept-5-ene-2,3-dicarboximide hemioxalate
Melting point: 220° C. (dec.)

| Elemental analysis: for $C_{23}H_{29}N_3O_4 \cdot \frac{1}{2}C_2H_2O_4$ | | | |
|---|---|---|---|
| | C | H | N |
| Calculated (%): | 63.13 | 6.63 | 9.20 |
| Found (%) | 62.85 | 6.53 | 9.49 |

N-{2-Hydroxy-3-(4-methylpiperazin-1-yl)propyl}cis-cyclohex-4-ene-1,2-dicarboximide dimaleate
Melting point: 159°–161° C.

| Elemental analysis: for $C_{16}H_{25}N_3O_2 \cdot 2C_4H_4O_4$ | | | |
|---|---|---|---|
| | C | H | N |
| Calculated (%): | 53.42 | 6.18 | 7.79 |
| Found (%): | 53.12 | 5.93 | 7.71 |

N-{2-Hydroxy-3-(4-methylpiperazin-1-yl)propyl}cis-cyclohexane-1,2-dicarboximide dimaleate
Melting point: 156°–159° C.

| Elemental analysis: for $C_{16}H_{27}N_3O_3 \cdot 2C_4H_4O_4$ | | | |
|---|---|---|---|
| | C | H | N |
| Calculated (%): | 53.22 | 6.53 | 7.76 |
| Found (%): | 52.99 | 6.54 | 7.65 |

N-{2-Hydroxy-3-(4-methylpiperazin-1-yl)propyl}endo-cis-bicyclo[2,2,1]hept-5-ene-2,3-dicarboximide dimaleate
Melting point: 158°–161° C.

| Elemental analysis: for $C_{17}H_{25}N_3O_3 \cdot 2C_4H_4O_4$ | | | |
|---|---|---|---|
| | C | H | N |
| Calculated (%): | 54.43 | 6.04 | 7.62 |
| Found (%): | 54.15 | 5.97 | 7.53 |

N-[2-Hydroxy-3-{4-(2-pyrimidyl)hexahydro-1H-1,4-diazepin-1-yl}propyl]cis-cyclohex-4-ene-1,2-dicarboximide maleate
Melting point: 153°–156° C.

| Elemental analysis: for $C_{20}H_{27}N_5O_3 \cdot C_4H_4O_4$ | | | |
|---|---|---|---|
| | C | H | N |
| Calculated (%): | 57.47 | 6.23 | 13.97 |
| Found (%): | 57.27 | 6.17 | 13.69 |

N-[2-Hydroxy-3-{4-(2-pyrimidyl)hexahydro-1H-1,4-diazepin-1-yl}propyl]endo-cis-bicyclo[2,2,1]hept-5-ene-2,3-dicarboximide maleate
Melting point: 171°–173° C.

| Elemental analysis: for $C_{21}H_{27}N_5O_3 \cdot C_4H_4O_4$ | | | |
|---|---|---|---|
| | C | H | N |
| Calculated (%): | 58.47 | 6.08 | 13.64 |
| Found (%): | 58.72 | 6.19 | 13.58 |

N-[2-Hydroxy-3-{4-(2-pyridyl)hexahydro-1H-1,4-diazepin-1-yl}propyl]cis-cyclohex-4-ene-1,2-dicarboximide dimaleate
Melting point: 142°–145° C.

| Elemental analysis: for $C_{21}H_{28}N_4O_3 \cdot 2C_4H_4O_4$ | | | |
|---|---|---|---|
| | C | H | N |
| Calculated (%): | 56.48 | 5.90 | 9.09 |
| Found (%): | 56.37 | 5.92 | 8.99 |

N-[2-Hydroxy-3-{4-(2-pyridyl)hexahydro-1H-1,4-diazepin-1-yl}propyl]endo-cis-bicyclo[2,2,1]hept-5-ene-2,3-dicarboximide dimaleate
Melting point: 152°–155° C.

| Elemental analysis: for $C_{22}H_{28}N_4O_3 \cdot 2C_4H_4O_4$ | | | |
|---|---|---|---|
| | C | H | N |
| Calculated (%): | 57.31 | 5.78 | 8.91 |
| Found (%): | 57.36 | 5.83 | 8.91 |

N-{2-Hydroxy-3-(4-phenylhexahydro-1H-1,4-diazepin-1-yl)propyl}endo-cis-bicyclo[2,2,1]hept-5-ene-2,3-dicarboximide
Melting point: 124°–126° C.

| Elemental analysis: for $C_{23}H_{29}N_3O_3$ | | | |
|---|---|---|---|
| | C | H | N |
| Calculated (%): | 69.85 | 7.39 | 10.63 |
| Found (%): | 69.84 | 7.34 | 10.54 |

N-[2-Hydroxy-3-{4-(2-pyridyl)piperazin-1-yl}propyl]-2,2-dimethylsuccinimide
Melting point: 131°–132.5° C.

| Elemental analysis: for $C_{18}H_{26}N_4O_3$ | | | |
|---|---|---|---|
| | C | H | N |
| Calculated (%): | 62.39 | 7.58 | 16.17 |
| Found (%): | 62.33 | 7.57 | 16.05 |

N-[2-Hydroxy-3-(4-phenylpiperazin-1-yl)propyl]cis-cyclohex-4-ene-1,2-dicarboximide
Melting point: 153°–157° C.

| Elemental analysis: for $C_{21}H_{27}N_3O_3$ | | | |
|---|---|---|---|
| | C | H | N |
| Calculated (%): | 68.25 | 7.38 | 11.37 |
| Found (%): | 68.22 | 7.39 | 11.39 |

N-[2-Hydroxy-3-{4-(2-methylphenyl)piperazin-1-yl}propyl]endo-cis-bicyclo[2,2,1]hept-5-ene-2,3-dicarboximide
Melting point: 120°–125° C.

| Elemental analysis: for $C_{23}H_{29}N_3O_3$ | | | |
|---|---|---|---|
| | C | H | N |
| Calculated (%): | 69.83 | 7.40 | 10.62 |
| Found (%): | 69.88 | 7.44 | 10.65 |

N-[3-{4-<2-(4,6-Dimethyl)pyrimidyl>piperazin-1-yl}-2-hydroxypropyl]phthalimide
Melting point: 137°–140° C.

| Elemental analysis: for $C_{21}H_{25}N_5O_3$ | | | |
|---|---|---|---|
| | C | H | N |
| Calculated (%): | 63.76 | 6.38 | 17.71 |
| Found (%): | 63.75 | 6.36 | 17.80 |

The following compounds were obtained by procedures similar to those in Example 2.
N-[2-Acetoxy-3-{4-(2-pyridyl)piperazin-1-yl}propyl]-cis-cyclohexane-1,2-dicarboximide dimaleate
Melting point: 142°–145° C.

| Elemental analysis: for $C_{22}H_{30}N_4O_4 \cdot 2C_4H_4O_4$ | | | |
|---|---|---|---|
| | C | H | N |
| Calculated (%): | 55.71 | 5.93 | 8.66 |
| Found (%): | 55.60 | 5.88 | 8.78 |

N-[2-Propionyloxy-3-{4-(2-pyridyl)piperazin-1-yl}propyl]cis-cyclohex-4-ene-1,2-dicarboximide dimaleate
Melting point: 139°–142° C.

| Elemental analysis: for $C_{23}H_{30}N_4O_4 \cdot 2C_4H_4O_4$ | | | |
|---|---|---|---|
| | C | H | N |
| Calculated (%): | 56.52 | 5.83 | 8.51 |
| Found (%): | 56.42 | 5.76 | 8.50 |

N-[2-Acetoxy-3-{4-(2-pyridyl)piperazin-1-yl}propyl]-succinimide dimaleate
Melting point: 134°–136° C.

Elemental analysis: for $C_{18}H_{24}N_4O_4.2C_4H_4O_4$

|  | C | H | N |
|---|---|---|---|
| Calculated (%): | 52.69 | 5.45 | 9.45 |
| Found (%): | 52.43 | 5.41 | 9.49 |

N-[2-Propionyloxy-3-{4-(2-pyridyl)piperazin-1-yl}propyl]succinimide dimaleate
Melting point: 152°–154° C.

Elemental analysis: for $C_{19}H_{26}N_4O_4.2C_4H_4O_4$

|  | C | H | N |
|---|---|---|---|
| Calculated (%): | 53.45 | 5.66 | 9.23 |
| Found (%): | 53.41 | 5.79 | 9.21 |

N-[2-Acetoxy-3-{4-(2-pyridyl)piperazin-1-yl}propyl]endo-cis-bicyclo[2,2,1]hept-5-ene-2,3-dicarboximide dimaleate
Melting point: 167° C. (dec.)

Elemental analysis: for $C_{23}H_{28}N_4O_3.2C_4H_4O_4$

|  | C | H | N |
|---|---|---|---|
| Calculated (%): | 56.70 | 5.54 | 8.53 |
| Found (%): | 56.63 | 5.56 | 8.40 |

N-[2-Propionyloxy-3-{4-(2-pyridyl)piperazin-1-yl}propyl]endo-cis-bicyclo[2,2,1]hept-5-ene-2,3-dicarboximide dimaleate
Melting point: 153°–156° C.

Elemental analysis: for $C_{24}H_{30}N_4O_4.2C_4H_4O_4$

|  | C | H | N |
|---|---|---|---|
| Calculated (%): | 57.30 | 5.72 | 8.35 |
| Found (%): | 57.22 | 5.60 | 8.37 |

N-[2-Acetoxy-3-{4-(2-pyridyl)piperazin-1-yl}propyl]phthalimide dimaleate
Melting point: 173°–176° C.

Elemental analysis: for $C_{22}H_{24}N_4O_4.2C_4H_4O_4$

|  | C | H | N |
|---|---|---|---|
| Calculated (%): | 56.23 | 5.04 | 8.74 |
| Found (%): | 56.46 | 4.85 | 8.80 |

N-[2-Acetoxy-3-{4-(2-pyrimidyl)piperazin-1-yl}propyl]cis-cyclohex-4-ene-1,2-dicarboximide maleate
Melting point: 175° C. (dec.)

Elemental analysis: for $C_{21}H_{27}N_5O_4.C_4H_4O_4$

|  | C | H | N |
|---|---|---|---|
| Calculated (%): | 56.70 | 5.90 | 13.23 |
| Found (%): | 56.49 | 5.95 | 13.10 |

N-[2-Propionyloxy-3-{4-(2-pyrimidyl)piperazin-1-yl}propyl]cis-cyclohex-4-ene-1,2-dicarboximide maleate
Melting point: 178° C. (dec.)

Elemental analysis: for $C_{22}H_{29}N_5O_4.C_4H_4O_4$

|  | C | H | N |
|---|---|---|---|
| Calculated (%): | 57.45 | 6.12 | 12.89 |
| Found (%): | 57.71 | 6.11 | 12.90 |

N-[2-Acetoxy-3-{4-(2-pyrimidyl)piperazin-1-yl}propyl]cis-cyclohexane-1,2-dicarboximide maleate
Melting point: 189° C. (dec.)

Elemental analysis: for $C_{21}H_{29}N_5O_4.C_4H_4O_4$

|  | C | H | N |
|---|---|---|---|
| Calculated (%): | 56.47 | 6.26 | 13.17 |
| Found (%): | 56.70 | 6.21 | 13.31 |

N-[2-Acetoxy-3-{4-(2-pyrimidyl)piperazin-1-yl}propyl]endo-cis-bicyclo[2,2,1]hept-5-ene-2,3-dicarboximide maleate
Melting point: 169° C. (dec.)

Elemental analysis: for $C_{22}H_{27}N_5O_4.C_4H_4O_4$

|  | C | H | N |
|---|---|---|---|
| Calculated (%) | 57.66 | 5.77 | 12.93 |
| Found (%): | 57.42 | 5.66 | 12.78 |

N-[2-Acetoxy-3-{4-(3-chlorophenyl)piperazin-1-yl}propyl]endo-cis-bicyclo[2,2,1]hept-5-ene-2,3-dicarboximide
Melting point: 127°–130° C.

Elemental analysis: for $C_{24}H_{28}ClN_3O_4$

|  | C | H | N |
|---|---|---|---|
| Calculated (%): | 62.93 | 6.17 | 9.18 |
| Found (%): | 62.84 | 6.14 | 8.99 |

N-[2-Acetoxy-3-{4-(3-chlorophenyl)piperazin-1-yl}propyl]exo-cis-bicyclo[2,2,1]hept-5-ene-2,3-dicarboximide oxalate
Melting point: 112° C. (dec.)

Elemental analysis: for $C_{24}H_{28}ClN_3O_4.C_2H_2O_4$

|  | C | H | N |
|---|---|---|---|
| Calculated (%): | 56.98 | 5.53 | 7.67 |
| Found (%): | 56.79 | 5.72 | 7.50 |

N-[2-Acetoxy-3-{4-(3-chlorophenyl)piperazin-1-yl}propyl]cis-cyclohex-4-ene-1,2-dicarboximide oxalate
Melting point: 160° C. (dec.)

Elemental analysis: for $C_{23}H_{28}ClN_3O_4.C_2H_2O_4$

|  | C | H | N |
|---|---|---|---|
| Calculated (%): | 56.01 | 5.65 | 7.84 |
| Found (%): | 55.97 | 5.62 | 7.77 |

N-[2-Acetoxy-3-{4-(3-chlorophenyl)piperazin-1-yl}propyl]cis-cyclohexane-1,2-dicarboximide oxalate
Melting point: 143° C. (dec.)

| Elemental analysis: for $C_{23}H_{30}ClN_3O_4 \cdot C_2H_2O_4$ | | | |
|---|---|---|---|
| | C | H | N |
| Calculated (%): | 55.80 | 6.01 | 7.81 |
| Found (%): | 55.52 | 5.87 | 7.72 |

N-[2-Propionyloxy-3-{4-(2-pyridyl)piperazin-1-yl}propyl]phthalimide maleate
Melting point: 176°–178° C.

| Elemental analysis: for $C_{23}H_{26}N_4O_4 \cdot C_4H_4O_4$ | | | |
|---|---|---|---|
| | C | H | N |
| Calculated (%): | 60.20 | 5.62 | 10.40 |
| Found (%): | 60.55 | 5.52 | 10.44 |

N-[2-Acetoxy-3-{4-(3-chlorophenyl)piperazin-1-yl}propyl]phthalimide
Melting point: 141°–144° C.

| Elemental analysis: for $C_{23}H_{24}ClN_3O_4$ | | | |
|---|---|---|---|
| | C | H | N |
| Calculated (%): | 62.50 | 5.48 | 9.51 |
| Found (%): | 62.56 | 5.61 | 9.29 |

The following compounds were obtained by procedures similar to those in Example 3.

N-[2-Isobutyryloxy-3-{4-(2-pyridyl)piperazin-1-yl}propyl]cis-cyclohex-4-ene-1,2-dicarboximide dimaleate
Melting point: 136°–139° C.

| Elemental analysis: for $C_{24}H_{32}N_4O_4 \cdot 2C_4H_4O_4$ | | | |
|---|---|---|---|
| | C | H | N |
| Calculated (%): | 57.13 | 6.01 | 8.33 |
| Found (%): | 57.20 | 5.89 | 8.32 |

N-[2-n-Caproyloxy-3-{4-(2-pyridyl)piperazin-1-yl}propyl]cis-cyclohex-4-ene-1,2-dicarboximide dimaleate
Melting point: 146°–148° C.

| Elemental analysis: for $C_{26}H_{36}N_4O_4 \cdot 2C_4H_4O_4$ | | | |
|---|---|---|---|
| | C | H | N |
| Calculated (%): | 58.27 | 6.34 | 8.00 |
| Found (%): | 58.17 | 6.21 | 8.25 |

N-[2-Cyclohexylcarbonyloxy-3-{4-(2-pyridyl)piperazin-1-yl}propyl]cis-cyclohex-4-ene-1,2-dicarboximide dimaleate
Melting point: 157° C. (dec.)

| Elemental analysis: for $C_{27}H_{36}N_4O_4 \cdot 2C_4H_4O_4$ | | | |
|---|---|---|---|
| | C | H | N |
| Calculated (%): | 58.96 | 6.23 | 7.86 |
| Found (%): | 59.21 | 6.08 | 7.78 |

N-[2-n-Decanoyloxy-3-{4-(2-pyridyl)piperazin-1-yl}propyl]cis-cyclohex-4-ene-1,2-dicarboximide dimaleate
Melting point: 122°–125° C.

| Elemental analysis: for $C_{30}H_{44}N_4O_4 \cdot 2C_4H_4O_4$ | | | |
|---|---|---|---|
| | C | H | N |
| Calculated (%): | 60.29 | 6.94 | 7.40 |
| Found (%): | 60.50 | 6.97 | 7.50 |

N-[2-Palmitoyloxy-3-{4-(2-pyridyl)piperazin-1-yl}propyl]cis-cyclohex-4-ene-1,2-dicarboximide dimaleate
Melting point: 119°–122° C.

| Elemental analysis: for $C_{36}H_{56}N_4O_4 \cdot 2C_4H_4O_4$ | | | |
|---|---|---|---|
| | C | H | N |
| Calculated (%): | 62.83 | 7.68 | 6.66 |
| Found (%): | 62.56 | 7.87 | 6.70 |

N-[3-{4-(2-Pyridyl)piperazin-1-yl}-2-(10-undecenoyloxy)propyl]cis-cyclohex-4-ene-1,2-dicarboximide dimaleate
Melting point: 118°–120° C.

| Elemental analysis: for $C_{31}H_{44}N_4O_4 \cdot 2C_4H_4O_4$ | | | |
|---|---|---|---|
| | C | H | N |
| Calculated (%): | 60.91 | 6.83 | 7.29 |
| Found (%): | 61.01 | 6.73 | 7.30 |

N-[2-(trans-2-Nonenoyloxy)-3-{4-(2-pyridyl)piperazin-1-yl}propyl]cis-cyclohex-4-ene-1,2-dicarboximide dimaleate
Melting point: 123°–126° C.

| Elemental analysis: for $C_{29}H_{40}N_4O_4 \cdot 2C_4H_4O_4$ | | | |
|---|---|---|---|
| | C | H | N |
| Calculated (%): | 59.98 | 6.54 | 7.56 |
| Found (%): | 59.75 | 6.35 | 7.53 |

N-[2-Benzoyloxy-3-{4-(2-pyridyl)piperazin-1-yl}propyl]cis-cyclohex-4-ene-1,2-dicarboximide dimaleate
Melting point: 147° C. (dec.)

| Elemental analysis: for $C_{27}H_{30}N_4O_4 \cdot 2C_4H_4O_4$ | | | |
|---|---|---|---|
| | C | H | N |
| Calculated (%): | 59.48 | 5.43 | 7.93 |
| Found (%): | 59.78 | 5.51 | 8.04 |

N-[2-n-Octanoyloxy-3-{4-(2-pyridyl)piperazin-1-yl}propyl]cis-cyclohex-4-ene-1,2-dicarboximide dimaleate
Melting point: 116°–119° C.

| Elemental analysis: for $C_{28}H_{40}N_4O_4 \cdot 2C_4H_4O_4$ | | | |
|---|---|---|---|
| | C | H | N |
| Calculated (%): | 59.33 | 6.65 | 7.69 |
| Found (%): | 59.24 | 6.49 | 7.67 |

N-[2-Cinnamoyloxy-3-{4-(2-pyridyl)piperazin-1-yl}propyl]cis-cyclohex-4-ene-1,2-dicarboximide dimaleate
Melting point: 114°–117° C.

| Elemental analysis: for C29H32N4O4.2C4H4O4 | | | |
|---|---|---|---|
| | C | H | N |
| Calculated (%): | 60.64 | 5.51 | 7.64 |
| Found (%): | 60.36 | 5.38 | 7.56 |

N-[2-Isobutyryloxy-3-{4-(2-pyridyl)piperazin-1-yl}propyl]cis-cyclohexane-1,2-dicarboximide dimaleate
Melting point: 145°–147° C.

| Elemental analysis: for C24H34N4O4.2C4H4O4 | | | |
|---|---|---|---|
| | C | H | N |
| Calculated (%): | 56.95 | 6.28 | 8.30 |
| Found (%): | 56.77 | 6.28 | 8.46 |

N-[2-n-Caproyloxy-3-{4-(2-pyridyl)piperazin-1-yl}propyl]cis-cyclohexane-1,2-dicarboximide dimaleate
Melting point: 146°–148° C.

| Elemental analysis: for C26H38N4O4.2C4H4O4 | | | |
|---|---|---|---|
| | C | H | N |
| Calculated (%): | 58.11 | 6.61 | 7.97 |
| Found (%): | 58.09 | 6.65 | 8.00 |

N-[2-Cyclohexylcarbonyloxy-3-{4-(2-pyridyl)piperazin-1-yl}propyl]cis-cyclohexane-1,2-dicarboximide dimaleate
Melting point: 156°–158° C.

| Elemental analysis: for C27H38N4O4.2C4H4O4 | | | |
|---|---|---|---|
| | C | H | N |
| Calculated (%): | 58.80 | 6.49 | 7.83 |
| Found (%): | 58.71 | 6.26 | 7.97 |

N-[2-Palmitoyloxy-3-{4-(2-pyridyl)piperazin-1-yl}propyl]cis-cyclohexane-1,2-dicarboximide dimaleate
Melting point: 128°–131° C.

| Elemental analysis: for C36H58N4O4.2C4H4O4 | | | |
|---|---|---|---|
| | C | H | N |
| Calculated (%): | 62.68 | 7.91 | 6.65 |
| Found (%): | 62.55 | 8.02 | 6.64 |

N-[3-{4-(2-Pyridyl)piperazin-1-yl}-2-(10-undecenoyloxy)propyl]cis-cyclohexane-1,2-dicarboximide dimaleate
Melting point: 124°–127° C.

| Elemental analysis: for C31H46N4O4.2C4H4O4 | | | |
|---|---|---|---|
| | C | H | N |
| Calculated (%): | 60.75 | 7.07 | 7.27 |
| Found (%): | 61.02 | 7.10 | 7.35 |

N-[2-Isobutyryloxy-3-{4-(2-pyridyl)piperazin-1-yl}propyl]succinimide maleate
Melting point: 164°–165° C.

| Elemental analysis: for C20H28N4O4.C4H4O4 | | | |
|---|---|---|---|
| | C | H | N |
| Calculated (%): | 57.12 | 6.40 | 11.10 |
| Found (%): | 56.86 | 6.20 | 10.99 |

N-[2-n-Caproyloxy-3-{4-(2-pyridyl)piperazin-1-yl}propyl]succinimide dimaleate
Melting point: 149°–150° C.

| Elemental analysis: for C22H32N4O4.2C4H4O4 | | | |
|---|---|---|---|
| | C | H | N |
| Calculated (%): | 55.53 | 6.22 | 8.63 |
| Found (%): | 55.43 | 6.11 | 8.76 |

N-[2-Cyclohexylcarbonyloxy-3-{4-(2-pyridyl)piperazin-1-yl}propyl]succinimide maleate
Melting point: 167°–169° C.

| Elemental analysis: for C23H32N4O4.C4H4O4 | | | |
|---|---|---|---|
| | C | H | N |
| Calculated (%): | 59.53 | 6.67 | 10.28 |
| Found (%): | 59.31 | 6.38 | 10.19 |

N-[2-n-Decanoyloxy-3-{4-(2-pyridyl)piperazin-1-yl}propyl]succinimide dimaleate
Melting point: 136°–138° C.

| Elemental analysis: for C26H40N4O4.2C4H4O4 | | | |
|---|---|---|---|
| | C | H | N |
| Calculated (%): | 57.93 | 6.87 | 7.95 |
| Found (%): | 57.82 | 6.84 | 8.00 |

N-[2-Palmitoyloxy-3-{4-(2-pyridyl)piperazin-1-yl}propyl]succinimide dimaleate
Melting point: 133°–135° C.

| Elemental analysis: for C32H52N4O4.2C4H4O4 | | | |
|---|---|---|---|
| | C | H | N |
| Calculated (%): | 60.88 | 7.68 | 7.10 |
| Found (%): | 60.83 | 7.49 | 7.02 |

N-[3-{4-(2-pyridyl)piperazin-1-yl}-2-(10-undecenoyloxy)propyl]succinimide dimaleate
Melting point: 135°–136° C.

| Elemental analysis: for C27H40N4O4.2C4H4O4 | | | |
|---|---|---|---|
| | C | H | N |
| Calculated (%): | 58.63 | 6.76 | 7.81 |
| Found (%): | 58.90 | 6.71 | 7.92 |

N-[2-(trans-2-Nonenoyloxy)-3-{4-(2-pyridyl)piperazin-1-yl}propyl]succinimide dimaleate
Melting point: 147°–149° C.

| Elemental analysis: for C25H36N4O4.2C4H4O4 | | | |
|---|---|---|---|
| | C | H | N |
| Calculated (%): | 57.53 | 6.45 | 8.13 |
| Found (%): | 57.60 | 6.43 | 8.17 |

N-[2-Benzoyloxy-3-{4-(2-pyridyl)piperazin-1-yl}propyl]succinimide dimaleate
Melting point: 174°–177° C.

| Elemental analysis: for $C_{23}H_{26}N_4O_4 \cdot 2C_4H_4O_4$ | | | |
|---|---|---|---|
| | C | H | N |
| Calculated (%): | 56.86 | 5.24 | 8.55 |
| Found (%) | 56.94 | 5.38 | 8.57 |

N-[2-n-Octanoyloxy-3-{4-(2-pyridyl)piperazin-1-yl}propyl]succinimide dimaleate
Melting point: 130°–131° C.

| Elemental analysis: for $C_{24}H_{36}N_4O_4 \cdot 2C_4H_4O_4$ | | | |
|---|---|---|---|
| | C | H | N |
| Calculated (%): | 56.78 | 6.56 | 8.28 |
| Found (%): | 56.61 | 6.52 | 8.29 |

N-[2-Isobutyryloxy-3-{4-(2-pyridyl)piperazin-1-yl}propyl]endo-cis-bicyclo[2,2,1]hept-5-ene-2,3-dicarboximide dimaleate
Melting point: 147°–150° C.

| Elemental analysis: for $C_{25}H_{32}N_4O_4 \cdot 2C_4H_4O_4$ | | | |
|---|---|---|---|
| | C | H | N |
| Calculated (%): | 57.88 | 5.90 | 8.18 |
| Found (%): | 57.61 | 5.69 | 8.14 |

N-[2-n-Caproyloxy-3-{4-(2-pyridyl)piperazin-1-yl}propyl]endo-cis-bicyclo[2,2,1]hept-5-ene-2,3-dicarboximide dimaleate
Melting point: 146°–148° C.

| Elemental analysis: for $C_{27}H_{36}N_4O_4 \cdot 2C_4H_4O_4$ | | | |
|---|---|---|---|
| | C | H | N |
| Calculated (%): | 58.98 | 6.24 | 7.86 |
| Found (%): | 58.81 | 6.04 | 7.84 |

N-[2-Cyclohexylcarbonyloxy-3-{4-(2-pyridyl)piperazin-1-yl}propyl]endo-cis-bicyclo[2,2,1]hept-5-ene-2,3-dicarboximide dimaleate
Melting point: 173°–175° C.

| Elemental analysis: for $C_{28}H_{36}N_4O_4 \cdot 2C_4H_4O_4$ | | | |
|---|---|---|---|
| | C | H | N |
| Calculated (%): | 59.65 | 6.13 | 7.73 |
| Found (%): | 59.50 | 6.17 | 7.76 |

N-[2-n-Decanoyloxy-3-{4-(2-pyridyl)piperazin-1-yl}propyl]endo-cis-bicyclo[2,2,1]hept-5-ene-2,3-dicarboximide dimaleate
Melting point: 112°–116° C.

| Elemental analysis: for $C_{31}H_{44}N_4O_4 \cdot 2C_4H_4O_4$ | | | |
|---|---|---|---|
| | C | H | N |
| Calculated (%): | 60.91 | 6.83 | 7.29 |
| Found (%): | 61.11 | 6.89 | 7.30 |

N-[2-(trans-2-Nonenoyloxy)-3-{4-(2-pyridyl)piperazin-1-yl}propyl]endo-cis-bicyclo[2,2,1]hept-5-ene-2,3-dicarboximide dimaleate
Melting point: 130°–132° C.

| Elemental analysis: for $C_{30}H_{40}N_4O_4 \cdot 2C_4H_4O_4$ | | | |
|---|---|---|---|
| | C | H | N |
| Calculated (%): | 60.62 | 6.44 | 7.44 |
| Found (%) | 60.83 | 6.40 | 7.46 |

N-[2-n-Octanoyloxy-3-{4-(2-pyridyl)piperazin-1-yl}propyl]endo-cis-bicyclo[2,2,1]hept-5-ene-2,3-dicarboximide dimaleate
Melting point: 106°–110° C.

| Elemental analysis: for $C_{29}H_{40}N_4O_4 \cdot 2C_4H_4O_4$ | | | |
|---|---|---|---|
| | C | H | N |
| Calculated (%): | 60.00 | 6.54 | 7.56 |
| Found (%): | 59.97 | 6.58 | 7.58 |

N-[2-Cinnamoyloxy-3-{4-(2-pyridyl)piperazin-1-yl}propyl]endo-cis-bicyclo[2,2,1]hept-5-ene-2,3-dicarboximide dimaleate
Melting point: 120°–123° C.

| Elemental analysis: for $C_{30}H_{32}N_4O_4 \cdot 2C_4H_4O_4$ | | | |
|---|---|---|---|
| | C | H | N |
| Calculated (%): | 61.27 | 5.42 | 7.53 |
| Found (%): | 61.27 | 5.51 | 7.45 |

N-[2-Isobutyryloxy-3-{4-(2-pyridyl)piperazin-1-yl}propyl]phthalimide maleate
Melting point: 174°–175° C.

| Elemental analysis: for $C_{24}H_{28}N_4O_4 \cdot C_4H_4O_4$ | | | |
|---|---|---|---|
| | C | H | N |
| Calculated (%): | 60.85 | 5.84 | 10.14 |
| Found (%): | 60.97 | 5.89 | 10.06 |

N-[2-n-Caproyloxy-3-{4-(2-pyridyl)piperazin-1-yl}propyl]phthalimide dimaleate
Melting point: 165°–166° C.

| Elemental analysis: for $C_{26}H_{32}N_4O_4 \cdot 2C_4H_4O_4$ | | | |
|---|---|---|---|
| | C | H | N |
| Calculated (%): | 58.60 | 5.79 | 8.04 |
| Found (%): | 58.78 | 5.58 | 8.05 |

N-[2-Cyclohexylcarbonyloxy-3-{4-(2-pyridyl)piperazin-1-yl}propyl]phthalimide maleate
Melting point: 135°–137° C.

| Elemental analysis: for $C_{27}H_{32}N_4O_4 \cdot C_4H_4O_4$ | | | |
|---|---|---|---|
| | C | H | N |
| Calculated (%): | 62.81 | 6.13 | 9.45 |
| Found (%): | 63.09 | 6.15 | 9.38 |

N-[2-n-Decanoyloxy-3-{4-(2-pyridyl)piperazin-1-yl}propyl]phthalimide dimaleate
Melting point: 138°–140° C.

| Elemental analysis: for $C_{30}H_{40}N_4O_4 \cdot 2C_4H_4O_4$ | | | |
|---|---|---|---|
| | C | H | N |
| Calculated (%): | 60.61 | 6.43 | 7.44 |

-continued

Elemental analysis: for $C_{30}H_{40}N_4O_4 \cdot 2C_4H_4O_4$

|  | C | H | N |
|---|---|---|---|
| Found (%): | 60.75 | 6.48 | 7.53 |

N-[2-Palmitoyloxy-3-{4-(2-pyridyl)piperazin-1-yl}propyl]phthalimide dimaleate
Melting point: 134°–136° C.

Elemental analysis: for $C_{36}H_{52}N_4O_4 \cdot 2C_4H_4O_4$

|  | C | H | N |
|---|---|---|---|
| Calculated (%): | 63.12 | 7.23 | 6.69 |
| Found (%): | 63.02 | 7.11 | 6.74 |

N-[3-{4-(2-Pyridyl)piperazin-1-yl}-2-(10-undecenoyloxy)propyl]phthalimide maleate
Melting point: 157°–159° C.

Elemental analysis: for $C_{31}H_{40}N_4O_4 \cdot 2C_4H_4O_4$

|  | C | H | N |
|---|---|---|---|
| Calculated (%): | 61.23 | 6.33 | 7.32 |
| Found (%): | 60.96 | 6.33 | 7.60 |

N-[2-(trans-2-Nonenoyloxy)-3-{4-(2-pyridyl)piperazin-1-yl}propyl]phthalimide maleate
Melting point: 138°–140° C.

Elemental analysis: for $C_{29}H_{36}N_4O_4 \cdot C_4H_4O_4$

|  | C | H | N |
|---|---|---|---|
| Calculated (%): | 63.84 | 6.50 | 9.02 |
| Found (%): | 63.54 | 6.44 | 8.93 |

N-[2-Benzoyloxy-3-{4-(2-pyridyl)piperazin-1-yl}propyl]phthalimide dimaleate
Melting point: 195° C. (dec.)

Elemental analysis: for $C_{27}H_{26}N_4O_4 \cdot 2C_4H_4O_4$

|  | C | H | N |
|---|---|---|---|
| Calculated (%): | 59.81 | 4.88 | 7.97 |
| Found (%): | 59.77 | 4.81 | 7.97 |

N-[2-n-Octanoyloxy-3-{4-(2-pyridyl)piperazin-1-yl}propyl]phthalimide dimaleate
Melting point: 135°–137° C.

Elemental analysis: for $C_{28}H_{36}N_4O_4 \cdot 2C_4H_4O_4$

|  | C | H | N |
|---|---|---|---|
| Calculated (%): | 59.64 | 6.13 | 7.73 |
| Found (%): | 59.81 | 6.08 | 7.80 |

N-[2-Cinnamoyloxy-3-{4-(2-pyridyl)piperazin-1-yl}propyl]phthalimide dimaleate
Melting point: 159°–162° C.

Elemental analysis: for $C_{29}H_{28}N_4O_4 \cdot 2C_4H_4O_4$

|  | C | H | N |
|---|---|---|---|
| Calculated (%): | 60.98 | 4.99 | 7.69 |
| Found (%): | 61.10 | 4.90 | 7.74 |

N-[2-n-Caproyloxy-3-{4-(2-pyridyl)piperazin-1-yl}propyl]endo-cis-bicyclo[2,2,2]oct-5-ene-2,3-dicarboximide dimaleate
Melting point: 138°–140° C.

Elemental analysis: for $C_{28}H_{38}N_4O_4 \cdot 2C_4H_4O_4$

|  | C | H | N |
|---|---|---|---|
| Calculated (%): | 59.49 | 6.39 | 7.71 |
| Found (%): | 59.43 | 6.15 | 7.69 |

N-[2-Cyclohexylcarbonyloxy-3-{4-(2-pyridyl)piperazin-1-yl}propyl]endo-cis-bicyclo[2,2,2]oct-5-ene-2,3-dicarboximide dimaleate
Melting point: 150°–152° C.

Elemental analysis: for $C_{29}H_{38}N_4O_4 \cdot 2C_4H_4O_4$

|  | C | H | N |
|---|---|---|---|
| Calculated (%): | 60.14 | 6.29 | 7.58 |
| Found (%): | 60.14 | 6.34 | 7.68 |

N-[2-n-Caproyloxy-3-{4-(2-pyridyl)piperazin-1-yl}propyl]endo-cis-bicyclo[2,2,1]heptane-2,3-dicarboximide dimaleate
Melting point: 132°–134° C.

Elemental analysis: for $C_{27}H_{38}N_4O_4 \cdot 2C_4H_4O_4$

|  | C | H | N |
|---|---|---|---|
| Calculated (%): | 58.80 | 6.50 | 7.84 |
| Found (%): | 58.77 | 6.49 | 7.84 |

N-[2-n-Caproyloxy-3-{4-(2-pyridyl)piperazin-1-yl}propyl]endo-cis-7-oxabicyclo[2,2,1]heptane-2,3-dicarboximide dimaleate
Melting point: 157°–158° C.

Elemental analysis: for $C_{26}H_{36}N_4O_5 \cdot 2C_4H_4O_4$

|  | C | H | N |
|---|---|---|---|
| Calculated (%): | 56.96 | 6.20 | 7.82 |
| Found (%): | 56.97 | 6.18 | 7.80 |

N-[2-Cyclohexylcarbonyloxy-3-{4-(2-pyridyl)piperazin-1-yl}propyl]endo-cis-7-oxabicyclo[2,2,1]heptane-2,3-dicarboximide dimaleate
Melting point: 175°–177° C.

Elemental analysis: for $C_{27}H_{34}N_4O_5 \cdot 2C_4H_4O_4$

|  | C | H | N |
|---|---|---|---|
| Calculated (%): | 57.67 | 6.10 | 7.69 |
| Found (%): | 57.66 | 6.12 | 7.68 |

N-[2-Isobutyryloxy-3-{4-(2-pyrimidyl)piperazin-1-yl}propyl]cis-cyclohex-4-ene-1,2-dicarboximide maleate
Melting point: 178° C. (dec.)

Elemental analysis: for $C_{23}H_{31}N_5O_4 \cdot C_4H_4O_4$

|  | C | H | N |
|---|---|---|---|
| Calculated (%): | 58.14 | 6.33 | 12.56 |
| Found (%): | 58.40 | 6.19 | 12.40 |

N-[2-n-Caproyloxy-3-{4-(2-pyrimidyl)piperazin-1-yl}propyl]cis-cyclohex-4-ene-1,2-dicarboximide maleate
Melting point: 145°–147° C.

| Elemental analysis: for $C_{25}H_{35}N_5O_4 \cdot C_4H_4O_4$ | | | |
|---|---|---|---|
| | C | H | N |
| Calculated (%): | 59.47 | 6.71 | 11.96 |
| Found (%): | 59.35 | 6.92 | 11.68 |

N-[2-Cyclohexylcarbonyloxy-3-{4-(2-pyrimidyl)piperazin-1-yl}propyl]cis-cyclohex-4-ene-1,2-dicarboximide maleate
Melting point: 173°–174° C.

| Elemental analysis: for $C_{26}H_{35}N_5O_4 \cdot C_4H_4O_4$ | | | |
|---|---|---|---|
| | C | H | N |
| Calculated (%): | 60.27 | 6.58 | 11.71 |
| Found (%): | 60.56 | 6.53 | 11.56 |

N-[2-Benzoyloxy-3-{4-(2-pyrimidyl)piperazin-1-yl}propyl]cis-cyclohex-4-ene-1,2-dicarboximide maleate
Melting point: 193° C. (dec.)

| Elemental analysis: for $C_{26}H_{29}N_5O_4 \cdot C_4H_4O_4$ | | | |
|---|---|---|---|
| | C | H | N |
| Calculated (%): | 60.90 | 5.62 | 11.84 |
| Found (%): | 60.92 | 5.54 | 11.87 |

N-[2-Isobutyryloxy-3-{4-(2-pyrimidyl)piperazin-1-yl}propyl]cis-cyclohexane-1,2-dicarboximide maleate
Melting point: 154°–155° C.

| Elemental analysis: for $C_{23}H_{33}N_5O_4 \cdot C_4H_4O_4$ | | | |
|---|---|---|---|
| | C | H | N |
| Calculated (%): | 57.93 | 6.67 | 12.51 |
| Found (%): | 58.06 | 6.85 | 12.46 |

N-[2-Cyclohexylcarbonyloxy-3-{4-(2-pyrimidyl)piperazin-1-yl}propyl]cis-cyclohexane-1,2-dicarboximide
Melting point: 169°–171° C.

| Elemental analysis: for $C_{26}H_{37}N_5O_4 \cdot C_4H_4O_4$ | | | |
|---|---|---|---|
| | C | H | N |
| Calculated (%): | 60.07 | 6.90 | 11.67 |
| Found (%): | 60.15 | 7.19 | 11.58 |

N-[2-n-Caproyloxy-3-{4-(3-chlorophenyl)piperazin-1-yl}propyl]endo-cis-bicyclo[2,2,1]hept-5-ene-2,3-dicarboximide oxalate
Melting point: 154° C. (dec.)

| Elemental analysis: for $C_{28}H_{36}ClN_3O_4 \cdot C_2H_2O_4$ | | | |
|---|---|---|---|
| | C | H | N |
| Calculated (%): | 59.64 | 6.35 | 6.96 |
| Found (%): | 59.34 | 6.19 | 6.99 |

N-[2-Benzoyloxy-3-{4-(3-chlorophenyl)piperazin-1-yl}propyl]endo-cis-bicyclo[2,2,1]hept-5-ene-2,3-dicarboximide oxalate
Melting point: 190° C. (dec.)

| Elemental analysis: for $C_{29}H_{30}ClN_3O_4 \cdot C_2H_2O_4$ | | | |
|---|---|---|---|
| | C | H | N |
| Calculated (%): | 61.02 | 5.30 | 6.89 |
| Found (%): | 61.28 | 5.14 | 6.60 |

N-{2-Isobutyryloxy-3-(4-methylpiperazin-1-yl)propyl}cis-cyclohex-4-ene-1,2-dicarboximide dimaleate
Melting point: 178°–180° C.

| Elemental analysis: for $C_{20}H_{31}N_3O_4 \cdot 2C_4H_4O_4$ | | | |
|---|---|---|---|
| | C | H | N |
| Calculated (%): | 55.15 | 6.46 | 6.89 |
| Found (%): | 54.98 | 6.46 | 6.84 |

N-{2-n-Caproyloxy-3-(4-methylpiperazin-1-yl)propyl}cis-cyclohex-4-ene-1,2-dicarboximide dimaleate
Melting point: 181° C. (dec.)

| Elemental analysis: for $C_{22}H_{35}N_3O_4 \cdot 2C_4H_4O_4$ | | | |
|---|---|---|---|
| | C | H | N |
| Calculated (%): | 56.49 | 6.81 | 6.59 |
| Found (%): | 56.39 | 6.80 | 6.60 |

N-{2-Isobutyryloxy-3-(4-methylpiperazin-1-yl)propyl}cis-cyclohexane-1,2-dicarboximide dimaleate
Melting point: 174° C. (dec.)

| Elemental analysis: for $C_{20}H_{33}N_3O_4 \cdot 2C_4H_4O_4$ | | | |
|---|---|---|---|
| | C | H | N |
| Calculated (%): | 54.97 | 6.77 | 6.87 |
| Found (%): | 54.93 | 6.68 | 6.92 |

N-{2-n-Caproyloxy-3-(4-methylpiperazin-1-yl)propyl}cis-cyclohexane-1,2-dicarboximide dimaleate
Melting point: 176° C. (dec.)

| Elemental analysis: for $C_{22}H_{37}N_3O_4 \cdot 2C_4H_4O_4$ | | | |
|---|---|---|---|
| | C | H | N |
| Calculated (%): | 56.32 | 7.10 | 6.57 |
| Found (%): | 56.52 | 7.26 | 6.57 |

N-{2-n-Caproyloxy-3-(4-methylpiperazin-1-yl)propyl}endo-cis-bicyclo[2,2,1]hept-5-ene-2,3-dicarboximide dimaleate
Melting point: 180°–182° C.

| Elemental analysis: for $C_{23}H_{35}N_3O_4 \cdot 2C_4H_4O_4$ | | | |
|---|---|---|---|
| | C | H | N |
| Calculated (%): | 57.30 | 6.68 | 6.47 |
| Found (%): | 57.17 | 6.85 | 6.33 |

N-{2-n-Caproyloxy-3-{4-(2-pyridyl)hexahydro-1H-1,4-diazepin-1-yl}propyl]cis-cyclohex-4-ene-1,2-dicarboximide dimaleate
Melting point: 98°–101° C.

| Elemental analysis: for $C_{27}H_{38}N_4O_4 \cdot 2C_4H_4O_4$ | | | |
|---|---|---|---|
| | C | H | N |
| Calculated (%): | 58.81 | 6.50 | 7.84 |

| Elemental analysis: for $C_{27}H_{38}N_4O_4 \cdot 2C_4H_4O_4$ | | | |
|---|---|---|---|
| | C | H | N |
| Found (%): | 58.69 | 6.49 | 7.80 |

N-[2-(3-Phenylpropionyloxy)-3-{4-(2-pyridyl)piperazin-1-yl}propyl]endo-cis-bicyclo[2,2,1]hept-5-ene-2,3-dicarboximide dimaleate
Melting point: 122°–124° C.

| Elemental analysis: for $C_{30}H_{34}N_4O_4 \cdot 2C_4H_4O_4$ | | | |
|---|---|---|---|
| | C | H | N |
| Calculated (%): | 61.11 | 5.68 | 7.50 |
| Found (%): | 60.92 | 5.65 | 7.42 |

N-[2-(3-Phenylpropionyloxy)-3-{4-(2-pyridyl)piperazin-1-yl}propyl]cis-cyclohex-4-ene-1,2-dicarboximide dimaleate
Melting point: 124°–127° C.

| Elemental analysis: for $C_{29}H_{34}N_4O_4 \cdot 2C_4H_4O_4$ | | | |
|---|---|---|---|
| | C | H | N |
| Calculated (%): | 60.47 | 5.77 | 7.63 |
| Found (%): | 60.44 | 5.69 | 7.50 |

N-[2-n-Caproyloxy-3-{4-(2-pyridyl)hexahydro-1H-1,4-diazepin-1-yl}propyl]endo-cis-bicyclo[2,2,1]hept-5-ene-2,3-dicarboximide dimaleate
Melting point: 110°–113° C.

| Elemental analysis: for $C_{28}H_{38}N_4O_4 \cdot 2C_4H_4O_4$ | | | |
|---|---|---|---|
| | C | H | N |
| Calculated (%): | 59.49 | 6.39 | 7.71 |
| Found (%): | 59.26 | 6.50 | 7.62 |

N-[2-n-Caproyloxy-3{4-(2-(4,6-dimethyl)-pyrimidyl<piperazin-1-yl}propyl]phthalimide maleate
Melting point: 166°–167.5° C.

| Elemental analysis: for $C_{27}H_{35}N_5O_4 \cdot C_4H_4O_4$ | | | |
|---|---|---|---|
| | C | H | N |
| Calculated (%): | 61.05 | 6.46 | 11.48 |
| Found (%): | 60.63 | 6.47 | 11.33 |

N-[2-Cyclohexylcarbonyloxy-3-{4-(2-methylphenyl)-piperazin-1-yl}propyl]endo-cis-bicyclo[2,2,1]hept-5-ene-2,3-dicarboximide maleate
Melting point: 206.5° C. (dec.)

| Elemental analysis: for $C_{30}H_{39}N_3O_4 \cdot C_4H_4O_4$ | | | |
|---|---|---|---|
| | C | H | N |
| Calculated (%): | 65.67 | 6.98 | 6.75 |
| Found (%): | 65.04 | 6.92 | 6.57 |

N-{2-Cyclohexylcarbonyloxy-3-(4-phenylpiperazin-1-yl)propyl}cis-cyclohex-4-ene-1,2-dicarboximide maleate
Melting point: 167°–169° C.

| Elemental analysis: for $C_{28}H_{37}N_3O_4 \cdot C_4H_4O_4$ | | | |
|---|---|---|---|
| | C | H | N |
| Calculated (%): | 64.51 | 6.95 | 7.05 |
| Found (%): | 64.95 | 6.91 | 7.07 |

N-[2-Cyclohexylcarbonyloxy-3-{4-(2-pyridyl)piperazin-1-yl}propyl]2,2-dimethylsuccinimide dimaleate
Melting point: 150°–154° C.

| Elemental analysis: for $C_{25}H_{36}N_4O_4 \cdot 2C_4H_4O_4$ | | | |
|---|---|---|---|
| | C | H | N |
| Calculated (%): | 57.53 | 6.45 | 8.13 |
| Found (%): | 57.13 | 6.35 | 8.15 |

The following compounds were obtained by procedures similar to those in Example 4.

N-{3-(4-Methylpiperazin-1-yl)-2-nicotinyloxypropyl}endo-cis-bicyclo[2,2,1]hept-5-ene-2,3-dicarboximide dimaleate
Melting point: 178° C. (dec.)

| Elemental analysis: for $C_{23}H_{28}N_4O_4 \cdot 2C_4H_4O_4$ | | | |
|---|---|---|---|
| | C | H | N |
| Calculated (%): | 56.70 | 5.62 | 8.54 |
| Found (%): | 56.75 | 5.62 | 8.30 |

N-[2-Nicotinyloxy-3-{4-(2-pyridyl)piperazin-1-yl}propyl]phthalimide maleate
Melting point: 189° C. (dec.)

| Elemental analysis: for $C_{26}H_{25}N_5O_4 \cdot C_4H_4O_4$ | | | |
|---|---|---|---|
| | C | H | N |
| Calculated (%): | 61.31 | 4.98 | 11.92 |
| Found (%): | 61.20 | 4.92 | 11.86 |

N-[2-Nicotinyloxy-3-{4-(2-pyridyl)piperazin-1-yl}propyl]endo-cis-bicyclo[2,2,1]hept-5-ene-2,3-dicarboximide maleate
Melting point: 203° C. (dec.)

| Elemental analysis: for $C_{27}H_{29}N_5O_4 \cdot C_4H_4O_4$ | | | |
|---|---|---|---|
| | C | H | N |
| Calculated (%): | 61.68 | 5.51 | 11.60 |
| Found (%): | 61.79 | 5.39 | 11.64 |

N-[2-Nicotinyloxy-3-{4-(2-pyridyl)piperazin-1-yl}propyl]cis-cyclohexane-1,2-dicarboximide maleate
Melting point: 193° C. (dec.)

| Elemental analysis: for $C_{26}H_{31}N_5O_4 \cdot C_4H_4O_4$ | | | |
|---|---|---|---|
| | C | H | N |
| Calculated (%): | 60.70 | 5.94 | 11.80 |
| Found (%): | 60.90 | 6.01 | 11.85 |

N-[2-Nicotinyloxy-3-{4-(2-pyridyl)piperazin-1-yl}propyl]cis-cyclohex-4-ene-1,2-dicarboximide maleate
Melting point: 183° C. (dec.)

| Elemental analysis: for $C_{26}H_{29}N_5O_4 \cdot C_4H_4O_4$ | | | |
|---|---|---|---|
| | C | H | N |
| Calculated (%): | 60.90 | 5.62 | 11.84 |
| Found (%): | 61.09 | 5.56 | 11.83 |

The following compounds were obtained by procedures similar to those in Example 5.

N-[2-n-Butylaminocarbonyloxy-3-{4-(2-pyridyl)piperazin-1-yl}propyl]cis-cyclohex-4-ene-1,2-dicarboximide dimaleate
Melting point: 138°–141° C.

| Elemental analysis: for $C_{25}H_{35}N_5O_4 \cdot 2C_4H_4O_4$ | | | |
|---|---|---|---|
| | C | H | N |
| Calculated (%): | 56.48 | 6.19 | 9.98 |
| Found (%): | 56.25 | 6.11 | 9.83 |

The following compounds were obtained by procedures similar to those in Example 6.

N-[2-n-Decylaminocarbonyloxy-3-{4-(2-pyridyl)piperazin-1-yl}propyl]cis-cyclohex-4-ene-1,2-dicarboximide dimaleate
Melting point: 124°–127° C.

| Elemental analysis: for $C_{31}H_{47}N_5O_4 \cdot 2C_4H_4O_4$ | | | |
|---|---|---|---|
| | C | H | N |
| Calculated (%): | 59.59 | 7.07 | 8.91 |
| Found (%): | 59.57 | 7.13 | 8.88 |

N-[2-n-Decylaminocarbonyloxy-3-{4-(2-pyridyl)piperazin-1-yl}propyl]endo-cis-bicyclo[2,2,1]hept-5-ene-2,3-dicarboximide dimaleate
Melting point: 105°–108° C.

| Elemental analysis: for $C_{32}H_{47}N_5O_4 \cdot 2C_4H_4O_4$ | | | |
|---|---|---|---|
| | C | H | N |
| Calculated (%): | 60.20 | 6.96 | 8.78 |
| Found (%): | 59.98 | 7.00 | 8.73 |

N-[2-Cyclohexylaminocarbonyloxy-3-{4-(2-pyridyl)-piperazin-1-yl}propyl]endo-cis-bicyclo[2,2,1]hept-5-ene-2,3-dicarboximide maleate
Melting point: 147°–151° C.

| Elemental analysis: for $C_{28}H_{37}N_5O_4 \cdot C_4H_4O_4$ | | | |
|---|---|---|---|
| | C | H | N |
| Calculated (%): | 61.61 | 6.64 | 11.23 |
| Found (%): | 61.31 | 6.64 | 10.95 |

The following compounds were obtained by procedures similar to those in Example 7.

N-[2-Propionyloxy-3-{4-(2-pyridyl)piperazin-1-yl}propyl]phthalimide dihydrochloride
Melting point: 240°–242° C. (dec.)

| Elemental analysis: for $C_{23}H_{26}N_4O_4 \cdot 2HCl$ | | | |
|---|---|---|---|
| | C | H | N |
| Calculated (%): | 55.75 | 5.71 | 11.31 |
| Found (%): | 55.46 | 5.61 | 11.27 |

N-[2-n-Caproyloxy-3-{4-(2-pyridyl)piperazin-1-yl}propyl]endo-cis-bicyclo[2,2,1]hept-5-ene-2,3-dicarboximide dihydrochloride
Melting point: 242°–244° C. (dec.)

| Elemental analysis: for $C_{27}H_{36}N_4O_4 \cdot 2HCl$ | | | |
|---|---|---|---|
| | C | H | N |
| Calculated (%): | 58.58 | 6.93 | 10.12 |
| Found (%): | 58.88 | 6.68 | 9.84 |

N-[2-Cyclohexylcarbonyloxy-3-{4-(2-pyridyl)piperazin-1-yl}propyl]-cis-cyclohex-4-ene-1,2-dicarboximide dihydrochloride
Melting point: 237°–239° C. (dec.)

| Elemental analysis: for $C_{27}H_{36}N_4O_4 \cdot 2HCl$ | | | |
|---|---|---|---|
| | C | H | N |
| Calculated (%): | 58.58 | 6.93 | 10.12 |
| Found (%): | 58.73 | 7.07 | 9.88 |

N-[2-n-Decanoyloxy-3-{4-(2-pyridyl)piperazin-1-yl}propyl]cyclohexane-1,2-dicarboximide dihydrochloride
Melting point: 191°–196° C.

| Elemental analysis: for $C_{30}H_{36}N_4O_4 \cdot 2HCl$ | | | |
|---|---|---|---|
| | C | H | N |
| Calculated (%) | 60.08 | 8.08 | 9.34 |
| Found (%): | 59.79 | 8.15 | 9.25 |

N-[2-Palmitoyloxy-3-{4-(2-pyridyl)piperazin-1-yl)}propyl]endo-cis-bicyclo[2,2,1]hept-5-ene-2,3-dicarboximide dihydrochloride
Melting point: 186°–190° C.

| Elemental analysis: for $C_{37}H_{56}N_4O_4 \cdot 2HCl$ | | | |
|---|---|---|---|
| | C | H | N |
| Calculated (%): | 64.04 | 8.44 | 8.08 |
| Found (%): | 63.79 | 8.29 | 8.34 |

N-[2-Palmitoyloxy-3-{4-(2-pyridyl)piperazin-1-yl}propyl]phthalimide dihydrochloride
Melting point: 184°–188° C.

| Elemental analysis: for $C_{36}H_{52}N_4O_4 \cdot 2HCl$ | | | |
|---|---|---|---|
| | C | H | N |
| Calculated (%): | 63.78 | 8.05 | 8.27 |
| Found (%) | 63.57 | 7.98 | 8.31 |

N-[2-(trans-2-Nonenoyloxy)-3-{4-(2-pyridyl)piperazin-1-yl}propyl]-endo-cis-bicyclo[2,2,1]hept-5-ene-2,3-dicarboximide dihydrochloride
Melting point: 164°–168° C.

| Elemental analysis: for $C_{30}H_{40}N_4O_4 \cdot 2HCl$ | | | |
|---|---|---|---|
| | C | H | N |
| Calculated (%): | 60.69 | 7.15 | 9.44 |
| Found (%): | 60.49 | 7.11 | 9.38 |

Examples of preparations containing representative compounds of the present invention are illustrated below.

| Preparation Example 1 Tablets | |
|---|---|
| N—[2-Hydroxy-3-{4-(2-pyridyl)piperazin-1-yl}propyl]endo-cis-bicyclo[2,2,1]heptane-2,3-dicarboximide | 50 g |
| Corn starch | 10 g |
| Lactose | 65 g |
| Calcium carboxymethyl cellulose | 10 g |
| Polyvinylpyrrolidone | 5 g |
| Talc | 10 g |
| Microcrystalline cellulose | 50 g |

According to conventional manner, the above respective ingredients were mixed into a granular form, and compression molded to give tablets, each containing 200 mg.

| Preparation Example 2 Capsules | |
|---|---|
| N—[2-Palmitoyloxy-3-{4-(2-pyridyl)piperazin-1-yl}propyl]cis-cyclohex-4-ene-1,2-dicarboximide dimaleate | 50 g |
| Lactose | 45 g |
| Corn starch | 5 g |

Using the above formulation and according to conventional manner, capsules, each containing 100 mg, were produced.

We claim:

1. A carboximide derivative of the formula

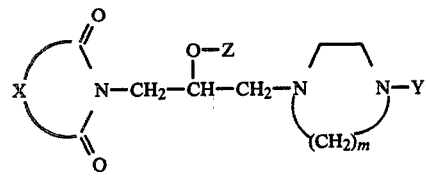

wherein X represents a group of the formula:

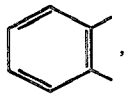

a group of the formula: 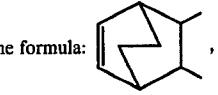, a group of the formula: 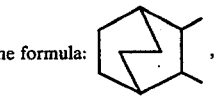, a group of the formula: 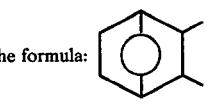, a group of the formula: 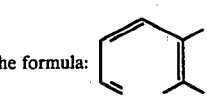, a group of the formula: 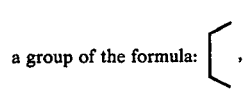, a group of the formula:

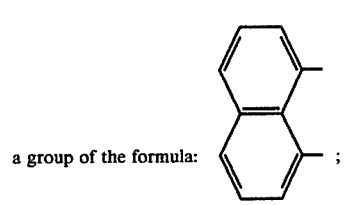 or a group of the formula: ;

Z represents a hydrogen atom or a group of the formula:

wherein R represents (1) alkyl of 1 to 16 carbon atoms, (2)

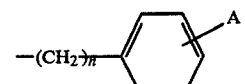

wherein n is an integer of 0-2 and A is H, methyl, methoxy or chlorine, (3) cyclopentyl, (4) cyclohexyl, (5) alkenyl of up to 16 carbon atoms, (6) cinnamoyl, (7) pyridyl or (8)

wherein $R_1$ is alkyl of up to 10 carbon atoms or cyclohexyl, and Y represents (1) alkyl of 1-6 carbon atoms, (2) phenyl, (3) phenyl substituted by methyl, methoxy, chlorine or trifluoromethyl, (4) pyridyl, (5) pyridyl substituted by methyl, methoxy or chlorine, (6) pyrimidyl, (7) pyrimidyl substituted by methyl or methoxy or (8) benzothiazolyl; and m represents an integer of 2 or 3, or a pharmaceutically acceptable salt thereof.

2. A carboximide derivative according to claim 1, wherein Y represents a substituted or unsubstituted pyridyl group as defined or a pharmaceutically acceptable salt thereof.

3. A carboximide derivative according to claim 1, wherein Y represents a substituted or unsubstituted pyrimidyl group as defined or a pharmaceutically acceptable salt thereof.

4. A carboximide derivative according to claim 1, wherein Y is 2-pyridyl or a pharmaceutically acceptable salt thereof.

5. A carboximide derivative according to claim 1, wherein Y is 2-pyridimyl or a pharmaceutically acceptable salt thereof.

6. A carboximide derivative according to claim 1, wherein X is

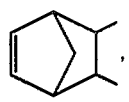

or a pharmaceutically acceptable salt thereof.

7. A carboximide derivative according to claim 1, wherein X is

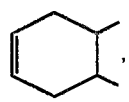

or a pharmaceutically acceptable salt thereof.

8. A carboximide derivative according to claim 1, wherein X is

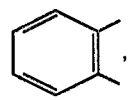

or a pharmaceutically acceptable salt thereof.

9. A carboximide derivative according to claim 1, wherein X is

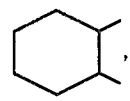

or a pharmaceutically acceptable salt thereof.

10. A carboximide derivative according to claim 1, wherein X is

or a pharmaceutically acceptable salt thereof.

11. A carboximide derivative according to claim 1, wherein X is

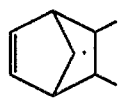

and Y is 2-pyridyl, or a pharmaceutically acceptable salt thereof.

12. A carboximide derivative according to claim 1, wherein X is

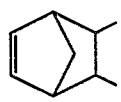

and Y is 2-pyrimidyl, or a pharmaceutically acceptable salt thereof.

13. A carboximide derivative according to claim 1, wherein X is

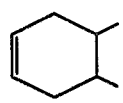

and Y is 2-pyridyl, or a pharmaceutically acceptable salt thereof.

14. A carboximide derivative according to claim 1, wherein X is

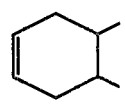

and Y is 2-pyrimidyl, or a pharmaceutically acceptable salt thereof.

15. A carboximide derivative according to claim 1, wherein X is

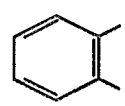

and Y is 2-pyridyl, or a pharmaceutically acceptable salt thereof.

16. A carboximide derivative according to claim 1, wherein X is

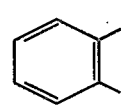

and Y is 2-pyrimidyl, or a pharmaceutically acceptable salt thereof.

17. A carboximide derivative according to claim 1, wherein X is

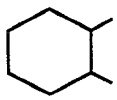

and Y is 2-pyridyl, or a pharmaceutically acceptable salt thereof.

18. A carboximide derivative according to claim 1, wherein X is

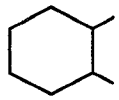

and Y is 2-pyrimidyl, or a pharmaceutically acceptable salt thereof.

19. A carboximide derivative according to claim 1, wherein X is

and Y is 2-pyridyl, or a pharmaceutically acceptable salt thereof.

20. A carboximide derivative according to claim 1, wherein X is

and Y is 2-pyrimidyl, or a pharmaceutically acceptable salt thereof.

21. A carboximide derivative according to claim 1, wherein Z represents a hydrogen atom, or a pharmaceutically acceptable salt thereof.

22. A carboximide derivative according to claim 1, wherein Z represents a group of the formula

wherein R is as defined in claim 48 or a pharmaceutically acceptable salt thereof.

23. N-[2-Cyclohexylcarbonyloxy-3-{4-(2-pyridyl)-piperazin-1-yl}propyl]endo-cis-bicyclo[2,2,1]hept-5-ene-2,3-dicarboximide or its pharmaceutically acceptable salt.

24. N-[2-n-Caproyloxy-3-{4-(2-pyridyl)piperazin-1-yl}propyl]cis-cyclohex-4-ene-1,2-dicarboximide or its pharmaceutically acceptable salt.

25. N-[2-Propionyloxy-3-{4-(2-pyridyl)piperazin-1-yl}propyl]phthalimide or its pharmaceutically acceptable salt.

26. N-[2-Nicotinyloxy-3-{4-(2-pyridyl)piperazin-1-yl}propyl]phthalimide or its pharmaceutically acceptable salt.

27. N-[2-(trans-2-Nonenoyloxy)-3-{4-(2-pyridyl)piperazin-1-yl}propyl]cis-cyclohex-4-ene-1,2-dicarboximide or its pharmaceutically acceptable salt.

28. N-[2-Palmitoyloxy-3-{4-(2-pyridyl)piperazin-1-yl}propyl]cis-cyclohex-4-ene-1,2-dicarboximide or its pharmaceutically acceptable salt.

29. N-[2-Cyclohexylcarbonyloxy-3-{4-(2-pyridyl)-piperazin-1-yl}propyl]cis-cyclohex-4-ene-1,2-dicarboximide or its pharmaceutically acceptable salt.

30. N-[2-n-Caproyloxy-3-{4-(2-pyridyl)piperazin-1-yl}propyl]phthalimide or its pharmaceutically acceptable salt.

31. N-[2-n-Octanoyloxy-3-{4-(2-pyridyl)piperazin-1-yl}propyl]succinimide or its pharmaceutically acceptable salt.

32. N-[2-Cyclohexylcarbonyloxy-3-{4-(2-pyridyl)-piperazin-1-yl}propyl]succinimide or its pharmaceutically acceptable salt.

33. N-[2-n-Decanoyloxy-3-{4-(2-pyridyl)piperazin-1-yl}propyl]cis-cyclohex-4-ene-1,2-dicarboximide or its pharmaceutically acceptable salt.

34. N-[2-Nicotinyloxy-3-{4-(2-pyridyl)piperazin-1-yl}propyl]cis-cyclohex-4-ene-1,2-dicarboximide or its pharmaceutically acceptable salt.

35. N-[2-Isobutyryloxy-3-{4-(2-pyridyl)piperazin-1-yl}propyl]cis-cyclohex-4-ene-1,2-dicarboximide or its pharmaceutically acceptable salt.

36. N-[2-n-Octanoyloxy-3-{4-(2-pyridyl)piperazin-1-yl}propyl]cis-cyclohex-4-ene-1,2-dicarboximide or its pharmaceutically acceptable salt.

37. N-[2-Cyclohexylcarbonyloxy-3-{4-(2-pyridyl)-piperazin-1-yl}propyl]cis-cyclohexane-1,2-dicarboximide or its pharmaceutically acceptable salt.

38. A pharmaceutical composition for treating diabetes which comprises an effective amount of a carboximide derivative as defined in claim 1 or a pharmaceutically acceptable salt thereof and a pharmaceutically acceptable carrier therefor.

39. A pharmaceutical composition for treating diabetes as claimed in claim 38, wherein Y represents a substituted or unsubstituted pyridyl group as defined.

40. A pharmaceutical composition for treating diabetes as claimed in claim 38 wherein Y is 2-pyridyl.

41. A pharmaceutical composition for treating diabetes as claimed in claim 38 wherein X is

and Y is 2-pyridyl.

42. A pharmaceutical composition for treating diabetes as claimed in claim 38 wherein Z is a group of the formula

as defined.

43. A method for treating diabetes which comprises administering to a patient suffering from diabetes an effective amount of a carboximide derivative or a pharmaceutically acceptable salt thereof according to claim 1.

* * * * *